(12) United States Patent
Lyngstadaas et al.

(10) Patent No.: US 7,304,030 B2
(45) Date of Patent: Dec. 4, 2007

(54) MATRIX PROTEIN COMPOSITION FOR DENTIN REGENERATION

(75) Inventors: Ståle Petter Lyngstadaas, Nesoddtangen (NO); Stina Gestrelius, Lund (SE)

(73) Assignee: Biora AB, Malmo (CH)

( * ) Notice: Subject to any disclaimer, the term of this patent is extended or adjusted under 35 U.S.C. 154(b) by 0 days.

(21) Appl. No.: 09/885,725

(22) Filed: Jun. 19, 2001

(65) Prior Publication Data
US 2005/0214231 A1    Sep. 29, 2005

Related U.S. Application Data

(60) Provisional application No. 60/213,790, filed on Jun. 23, 2000.

(30) Foreign Application Priority Data

Jun. 20, 2000  (DK) ................. 2000 00959
Nov. 8, 2000   (DK) ................. 2000 01665

(51) Int. Cl.
*A61K 38/00*  (2006.01)
*C07K 14/00*  (2006.01)
(52) U.S. Cl. .................. 514/2; 530/300; 424/435
(58) Field of Classification Search ...................... None
See application file for complete search history.

(56) References Cited

U.S. PATENT DOCUMENTS 6,300,062 B1 * 10/2001 Cerny et al. .............. 435/6
6,503,539 B2 *  1/2003 Gestrelius et al. .......... 424/549

FOREIGN PATENT DOCUMENTS

WO    WO 97/02730    1/1997
WO    WO 99/43344    9/1999

OTHER PUBLICATIONS

Nakamura, M. et al. Anat Rec. 238(3):383-396 (1994).*
Ruch, J.V. et al. Int. J. Dev. Biol. 39: 51-68 (1995).*
Sasaki, T. and Kido, H. Archs oral Biol. 40(3): 209-219 (1995).*
Cox et al., "Biocompatibility of various dental materials: pulp healing with surface seal", Int J Periodont Rest Dent 16: 241-251 (1996).*
Kiba et al., "Pulpal reactions to two experimental bonding systems for pulp capping procedures", Journal of Oral Sciences 42(2): 69-74 (2000).*
L. Hammarstrom: Enamel matrix, cementum development and regeneration *J. Clin. Periodontol. 1997*; 24: pp. 658-668.
Fincham et al., Self-Assembly of a Recombinant Amelogenin Protein Generates Supramolecular Structures. *J. Struct. Biol.* Mar.-Apr. 1994; 112(2):103-9.
Fincham et al., Evidence for Amelogenin "Nanospheres" as Functional Components of Secretory-State Enamel Matrix. *J. Struct. Biol.* Jul.-Aug. 1995; 115(1):50-9.
Gestrelius S. Andersson C, Johansson AC, Persson E, Brodin A, Rydhag L, Hammarstrom L (1997). Formulation of enamel matrix derivative for surface coating. Kinetics and cell colonization. *J. Clin Periodontol*, 24: 678-684.
Lyngstadaas SP, Lundberg E, Ekdahl H, Andersson C, Gestrelius S (2001). Autocrine growth factors in human periodontal ligament cells cultured on enamel matrix derivative. *J. Clin Periodontol*, Feb;28(2):181-8.
T. Inai et al.: "Demonstration of amelogenin in the enamel-free cusps of rat molar tooth germs: Immunofluorescent and immunoelectron microscopic studies." The Anatomical Record, vol. 233 No. 4, Aug. 1992, pp. 588-596.
James T. Mellonig; "Enamel Matrix Derivative for Periodontal Reconstructive Surgery; Technique and Clinical and Histologic Case Report" International Journal of Peridontics & Restorative Dentistry, vol. 19, No. 1, Feb. 1999, pp. 9-19.
A.R. Ten Cate: *Oral Histology, Development, sttructure and Function*, 3rd Ed., Mosby 1989, pp. 150-196.

* cited by examiner

*Primary Examiner*—Kathleen Kerr Bragdon
*Assistant Examiner*—Anand Desai
(74) *Attorney, Agent, or Firm*—Rissman Jobse Hendricks & Oliverio LLP

(57) ABSTRACT

The present invention relates to the surprising finding that enamel matrix, enamel matrix derivatives and/or enamel matrix proteins induce dentin regeneration. The invention thus relates to the use of a preparation of an active enamel substance for the preparation of a pharmaceutical composition for the formation or regeneration of dentin following dental procedures involving exposure of vital dental pulp tissue. In another aspect, the invention relates to a method of promoting the formation or regeneration of dentin following dental procedures involving exposure of vital dental pulp tissue, the method comprising applying an effective amount of an active enamel substance on exposed vital dental pulp tissue after dental procedures.

37 Claims, 24 Drawing Sheets

SEQUENCE LISTING

```
<160> NUMBER OF SEQ ID NOS: 6

<210> SEQ ID NO 1
<211> LENGTH: 407
<212> TYPE: PRT
<213> ORGANISM: rat

<400> SEQUENCE: 1

Met Ser Ala Ser Lys Ile Pro Leu Phe Lys Met Lys Gly Leu Leu Leu
1               5                   10                  15

Phe Leu Ser Leu Val Lys Met Ser Leu Ala Val Pro Ala Phe Pro Gln
            20                  25                  30

Gln Pro Gly Ala Gln Gly Met Ala Pro Pro Gly Met Ala Ser Leu Ser
        35                  40                  45

Leu Glu Thr Met Arg Gln Leu Gly Ser Leu Gln Gly Leu Asn Ala Leu
    50                  55                  60

Ser Gln Tyr Ser Arg Leu Gly Phe Gly Lys Ala Leu Asn Ser Leu Trp
65                  70                  75                  80

Leu His Gly Leu Leu Pro Pro His Asn Ser Phe Pro Trp Ile Gly Pro
                85                  90                  95

Arg Glu His Glu Thr Gln Gln Pro Ser Leu Gln Pro His Gln Pro Gly
            100                 105                 110

Leu Lys Pro Phe Leu Gln Pro Thr Ala Ala Thr Gly Val Gln Val Thr
        115                 120                 125

Pro Gln Lys Pro Gly Pro His Pro Pro Met His Pro Gly Gln Leu Pro
    130                 135                 140

Leu Gln Glu Gly Glu Leu Ile Ala Pro Asp Glu Pro Gln Val Ala Pro
145                 150                 155                 160

Ser Glu Asn Pro Pro Thr Pro Glu Val Pro Ile Met Asp Phe Ala Asp
                165                 170                 175

Pro Gln Phe Pro Thr Val Phe Gln Ile Ala His Ser Leu Ser Arg Gly
            180                 185                 190

Pro Met Ala His Asn Lys Val Pro Thr Phe Tyr Pro Gly Met Phe Tyr
        195                 200                 205

Met Ser Tyr Gly Ala Asn Gln Leu Asn Ala Pro Gly Arg Ile Gly Phe
    210                 215                 220
```

```
Met Ser Ser Glu Glu Met Pro Gly Glu Arg Gly Ser Pro Met Ala Tyr
225                 230                 235                 240

Gly Thr Leu Phe Pro Gly Tyr Gly Gly Phe Arg Gln Thr Leu Arg Gly
                245                 250                 255

Leu Asn Gln Asn Ser Pro Lys Gly Gly Asp Phe Thr Val Glu Val Asp
            260                 265                 270

Ser Pro Val Ser Val Thr Lys Gly Pro Glu Lys Gly Glu Gly Pro Glu
        275                 280                 285

Gly Ser Pro Leu Gln Glu Ala Ser Pro Asp Lys Gly Glu Asn Pro Ala
    290                 295                 300

Leu Leu Ser Gln Ile Ala Pro Gly Ala His Ala Gly Leu Leu Ala Phe
305                 310                 315                 320

Pro Asn Asp His Ile Pro Asn Met Ala Arg Gly Pro Ala Gly Gln Arg
                325                 330                 335

Leu Leu Gly Val Thr Pro Ala Ala Ala Asp Pro Leu Ile Thr Pro Glu
            340                 345                 350

Leu Ala Glu Val Tyr Glu Thr Tyr Gly Ala Asp Val Thr Thr Pro Leu
        355                 360                 365

Gly Asp Gly Glu Ala Thr Met Asp Ile Thr Met Ser Pro Asp Thr Gln
    370                 375                 380

Gln Pro Pro Met Pro Gly Asn Lys Val His Gln Pro Val His Asn
385                 390                 395                 400

Ala Trp Arg Phe Gln Glu Pro
                405

<210> SEQ ID NO 2
<211> LENGTH: 407
<212> TYPE: PRT
<213> ORGANISM: rat

<400> SEQUENCE: 2

Met Ser Ala Ser Lys Ile Pro Leu Phe Lys Met Lys Gly Leu Leu Leu
1               5                   10                  15

Phe Leu Ser Leu Val Lys Met Ser Leu Ala Val Pro Ala Phe Pro Gln
                20                  25                  30

Gln Pro Gly Ala Gln Gly Met Ala Pro Pro Gly Met Ala Ser Leu Ser
            35                  40                  45

Leu Glu Thr Met Arg Gln Leu Gly Ser Leu Gln Gly Leu Asn Ala Leu
        50                  55                  60

Ser Gln Tyr Ser Arg Leu Gly Phe Gly Lys Ala Leu Asn Ser Leu Trp
65                  70                  75                  80

Leu His Gly Leu Leu Pro Pro His Asn Ser Phe Pro Trp Ile Gly Pro
                85                  90                  95

Arg Glu His Glu Thr Gln Gln Pro Ser Leu Gln Pro His Gln Pro Gly
                100                 105                 110

Leu Lys Pro Phe Leu Gln Pro Thr Ala Ala Thr Gly Val Gln Val Thr
            115                 120                 125

Pro Gln Lys Pro Gly Pro Pro Pro Met His Pro Gly Gln Leu Pro
        130                 135                 140

Leu Gln Glu Gly Glu Leu Ile Ala Pro Asp Glu Pro Gln Val Ala Pro
145                 150                 155                 160

Ser Glu Asn Pro Pro Thr Pro Glu Val Pro Ile Met Asp Phe Ala Asp
                165                 170                 175

Pro Gln Phe Pro Thr Val Phe Gln Ile Ala His Ser Leu Ser Arg Gly
```

```
                180             185             190
Pro Met Ala His Asn Lys Val Pro Thr Phe Tyr Pro Gly Met Phe Tyr
        195                 200                 205
Met Ser Tyr Gly Ala Asn Gln Leu Asn Ala Pro Gly Arg Ile Gly Phe
    210                 215                 220
Met Ser Ser Glu Glu Met Pro Gly Glu Arg Gly Ser Pro Met Ala Tyr
225                 230                 235                 240
Gly Thr Leu Phe Pro Gly Tyr Gly Phe Arg Gln Thr Leu Arg Gly
                245                 250                 255
Leu Asn Gln Asn Ser Pro Lys Gly Gly Asp Phe Thr Val Glu Val Asp
            260                 265                 270
Ser Pro Val Ser Val Thr Lys Gly Pro Glu Lys Gly Glu Gly Pro Glu
        275                 280                 285
Gly Ser Pro Leu Gln Glu Ala Ser Pro Asp Lys Gly Glu Asn Pro Ala
    290                 295                 300
Leu Leu Ser Gln Ile Ala Pro Gly Ala His Ala Gly Leu Leu Ala Phe
305                 310                 315                 320
Pro Asn Asp His Ile Pro Asn Met Ala Arg Gly Pro Ala Gly Gln Arg
                325                 330                 335
Leu Leu Gly Val Thr Pro Ala Ala Asp Pro Leu Ile Thr Pro Glu
            340                 345                 350
Leu Ala Glu Val Tyr Glu Thr Tyr Gly Ala Asp Val Thr Thr Pro Leu
        355                 360                 365
Gly Asp Gly Glu Ala Thr Met Asp Ile Thr Met Ser Pro Asp Thr Gln
    370                 375                 380
Gln Pro Pro Met Pro Gly Asn Lys Val His Gln Pro Val His Asn
385                 390                 395                 400
Ala Trp Arg Phe Gln Glu Pro
                405

<210> SEQ ID NO 3
<211> LENGTH: 4
<212> TYPE: PRT
<213> ORGANISM: rat
<220> FEATURE:
<221> NAME/KEY: PEPTIDE
<222> LOCATION:
<223> OTHER INFORMATION: DGEA

<400> SEQUENCE: 3

Asp Gly Glu Ala
 1

<210> SEQ ID NO 4
<211> LENGTH: 4
<212> TYPE: PRT
<213> ORGANISM: rat
<220> FEATURE:
<221> NAME/KEY: PEPTIDE
<222> LOCATION:
<223> OTHER INFORMATION: VTKG

<400> SEQUENCE: 4

Val Thr Lys Gly
 1

<210> SEQ ID NO 5
<211> LENGTH: 4
<212> TYPE: PRT
<213> ORGANISM: rat
```

-continued

```
<220> FEATURE:
<221> NAME/KEY: PEPTIDE
<222> LOCATION:
<223> OTHER INFORMATION: EKGE

<400> SEQUENCE: 5

Glu Lys Gly Glu
 1

<210> SEQ ID NO 6
<211> LENGTH: 4
<212> TYPE: PRT
<213> ORGANISM: rat
<220> FEATURE:
<221> NAME/KEY: PEPTIDE
<222> LOCATION:
<223> OTHER INFORMATION: DKGE

<400> SEQUENCE: 6

Asp Lys Gly Glu
 1
```

MATRIX PROTEIN COMPOSITION FOR DENTIN REGENERATION

This application claims the benefit of U.S. Provisional Application No. 60/213,790, filed on Jun. 23, 2000.

FIELD OF INVENTION

The present invention relates to the use of enamel matrix, enamel matrix derivatives and/or enamel matrix proteins for dentin regeneration.

BACKGROUND OF THE INVENTION

Enamel matrix proteins such as those present in enamel matrix are well-known as precursors of dental enamel. Enamel matrix proteins and enamel matrix derivatives have previously been described in the literature to induce enamel formation (U.S. Pat. No. 4,672,032, Slavkin) or binding between different types of mineralised tissue such as cementum and bone (EP-B0 337 967 and EP-B-0 263 086). Furthermore, enamel matrix proteins and derivatives have been disclosed to promote wound healing in soft tissues such as skin and mucosa (WO 99/43344). The use of enamel matrix proteins or enamel matrix derivatives for dentin regeneration has not, to the inventors' knowledge, been reported previously.

Exposure of vital dental pulp is a common complication, either accidentally or by design, during normal dental restorative and prosthodontic procedures and also following crown fractures, trauma, and caries. Traditionally minimal exposures of dental pulp are treated either by applying a $Ca(OH)_2$ paste or a filling material (e.g. composites) directly onto the pulp to induce superficial necrosis sometimes followed by sclerotisation and reactive dentin formation deeper down in the pulp tissue. This strategy, however, seldom restores a mineralised barrier between the pulp and the restorative material(s) and in frequent cases the dental pulp becomes inflamed and has to be treated by pulpectomy (removal of the entire pulp) or pulpotomy (removal of a large portion of the pulp) and subsequent endodontic filling with synthetic materials (e.g. guttapercha). In the cases where a larger part of the pulp is exposed treatment always includes a pulpectomy and endodontic filling.

Endodontically treated teeth lose their blood supply, innervation and ability to produce reactive hard tissue (secondary dentin). As a result, these teeth become brittle and are also more prone to masticatory induced trauma and grave caries (due to lack of sensibility patients do not feel pain). This makes the lifespan of endodontically treated teeth much shorter than that of vital teeth and thus less useful as pillars for prosthodontic tooth replacements.

If a way to induce new dentin formation that efficiently can cover and seal off exposed dental pulp could be found, it would constitute a major breakthrough in conservative dentistry.

SUMMARY OF THE INVENTION

The present invention is based on the surprising finding that enamel matrix, enamel matrix derivatives or enamel matrix proteins (collectively termed "active enamel substance" in the following) are able to induce dentin formation in dental pulp cells.

Accordingly, the invention relates to the use of a preparation of an active enamel substance for the preparation of a pharmaceutical composition for the formation or regeneration of dentin following dental procedures involving exposure of vital dental pulp tissue.

In another aspect, the invention relates to a method of promoting the formation or regeneration of dentin following dental procedures involving exposure of vital dental pulp tissue, the method comprising applying an effective amount of an active enamel substance on exposed vital dental pulp tissue after dental procedures.

The observation that enamel matrix proteins are capable of inducing dentin formation in vital pulp tissue was first made in experiments with developing teeth where pulp cells were accidentally exposed to enamel matrix during a surgical procedure to remove the enamel organ from developing teeth in rats. The findings have later been confirmed by repeated experiments both in rats and pigs. Furthermore, the inventors have developed a tooth trauma model in adult pigs which confirms that the use of an enamel matrix protein composition is highly efficient in inducing hard tissue formation in the exposed dental pulp. That enamel proteins promotes dentin formation in developed pulp tissue is surprising since these proteins are only naturally present in developing teeth and never present in other tissues or in mature dental tissues (i.e. in adults or children of more than about 12 years of age).

Without wishing to be limited to any particular theory, It is assumed that because the action of these molecules during tooth formation is associated with the onset of mineralisation of both dentin and enamel, these proteins are likely to be part of a mechanism for dental hard tissue formation. Based on the present findings, it would appear that even though enamel matrix proteins are completely removed from dental tissue upon tooth development, cells in the adult dental pulp retain their ability to respond to these proteins by inducing dormant developmental processes for dentin formation.

It would appear that the mechanism by which enamel matrix proteins induce dentin formation differs significantly from the mechanism inducing cementum formation reported by L. Hammarström, *J. Clin. Periodontol.* 24, 1997, pp. 658-668, where application of enamel matrix proteins to experimental cavities drilled in exposed root surfaces resulted in the formation of cementum when the experimental teeth were replanted in contact with periodontal ligament. In the case reported by Hammarström, formation of cementum occurred directly on the surface of already formed hard tissue. According to the present invention, on the other hand, ectopic dentin is formed, i.e. enamel matrix proteins are able to stimulate formation of dentin at sites where no preexisting hard tissues are found.

The characteristic formation of new dentin induced in pulpal wounds by EMD as shown in the present invention, shows that EMD holds the potential for being used also for direct pulp capping in both traumatized and decayed teeth. Already on the market and approved for clinical applications, EMD could rapidly be used to expand the clinical indications for successful direct pulp capping procedures.

DETAILED DESCRIPTION OF THE INVENTION

Teeth are composed of three hard (mineralized) tissues, namely enamel, dentin and cementum, and centrally located soft tissue, called dental pulp. The dental pulp is mainly composed of fibroblasts and contains blood vessels and nerves. The dental pulp of a fully formed tooth (mature tooth) is enclosed by dentin on all sides except for a small foramen at the apical end of the root. Dentin is the major dental tissue and is formed by specific cells termed odontoblasts. Different types of dentin have been distinguished. Most of the dentin is formed during tooth development and is termed primary dentin. After the period of tooth development, some dentin formation continues but at a markedly slower rate. The dentin formed after tooth development is termed secondary dentin. Certain events such as occurrence of dental caries, cavity preparation and trauma may induce an accelerated form of dentin termed reactive, reparative or tertiary dentin. Morphologically, primary and secondary dentin is a non-cellular dental, mineralized tissue containing narrow canals called dentinal tubules extending from the pulp towards the periphery. Next to the pulp, there is a thin non-mineralized layer termed predentin. Reparative dentin may occasionally have a more irregular morphology with more irregular distribution of dentinal tubules. Occasionally, dentin may contain enclosed cells in which case it is termed osteodentin. For a further discussion of dental morphology, reference is made to A. R. Ten Cate, *Oral Histology. Development, Structure and Function,* 5th Ed., Mosby 1998, pp. 150-196).

As indicated above, it has surprisingly been found that the active enamel substance is capable of promoting the formation of reactive dentin in dental pulp tissue even in mature teeth (i.e. teeth of adults or children of more than about 12 years of age) which are not naturally exposed to enamel matrix or proteins present therein. In a particular embodiment, the invention therefore relates to the use of the active enamel substance for the regeneration of secondary dentin in vital dental pulp tissue. The regeneration of secondary dentin is particularly advantageous as secondary dentin has a structure closely resembling that of primary dentin, and the application of active enamel substance therefore participates in the restoration of dental pulp with a structural organisation giving it similar properties to the dental pulp originally formed in the tooth.

Alternatively, however, the active enamel substance is also useful for the formation of reparative dentin or osteodentin in vital dental pulp tissue, thereby ensuring a quick reparative process in the dental pulp although this results in the formation of dentin of a somewhat poorer quality than primary or secondary dentin as the composition and structure does not resemble that of primary dentin. The reparative process mainly occurs upon major dental trauma involving exposure of dental pulp, or upon major dental procedures such as pulpotomy or pulpectomy.

As indicated above, the use of the active enamel substance is particularly useful for promoting dentin formation or regeneration in vital dental pulp tissue in erupted teeth in which enamel matrix proteins are not naturally present in sufficient amounts to provide a healing effect following dental procedures. This is the case both for adults and children whose permanent teeth have developed.

The ability of the active enamel substance to promote or induce formation for dentin may also be exploited in association with cavity preparation, especially deep cavities where it is desirable to increase the thickness of the dentinal wall to avoid or reduce the risk of pulpal exposure, to avoid or reduce the exposure of the pulp to toxic or irritating substances, or to reduce or eliminate the hypersensitivity that often appears after dental treatment.

According to the present use, the preparation of active enamel substance is preferably applied onto dental pulp before application of a filling material following dental procedures involving exposure of vital dental pulp tissue. Pharmaceutical compositions suitable for such application are discussed below in further detail.

Enamel Matrix, Enamel Matrix Derivatives and Enamel Matrix Proteins

Enamel matrix is a precursor to enamel and may be obtained from any relevant natural source, i.e. a mammal in which teeth are under development. A suitable source is developing teeth from slaughtered animals such as, e.g., calves, pigs or lambs. Another source is for example fish skin.

Enamel matrix can be prepared from developing teeth as described previously (EP-B-0 337 967 and EP-B-0 263 086). The enamel matrix is scraped off and enamel matrix derivatives are prepared, e.g. by extraction with aqueous solution such as a buffer, a dilute acid or base or a water/solvent mixture, followed by size exclusion, desalting or other purification steps, optionally followed by freeze-drying. Enzymes may be deactivated by treatment with heat or solvents, in which case the derivatives may be stored in liquid form without freeze-drying.

In the present context, enamel matrix derivatives are derivatives of enamel matrix which include one or several enamel matrix proteins or parts of such proteins, produced naturally by alternate splicing or processing, or by either enzymatic or chemical cleavage of a natural length protein, or by synthesis of polypeptides in vitro or in vivo (recombinant DNA methods or cultivation of diploid cells). Enamel matrix protein derivatives also include enamel matrix related polypeptides or proteins. The polypeptides or proteins may be bound to a suitable biodegradable carrier molecule, such as polyamino acids or polysaccharides, or combinations thereof. Furthermore, the term enamel matrix derivatives also encompasses synthetic analogous substances.

Proteins are biological macromolecules constituted by amino acid residues linked together by peptide bonds. Proteins, as linear polymers of amino acids, are also called polypeptides. Typically, proteins have 20-800 amino acid residues and hence have molecular weights in the range of from about 6,000 to about several hundred thousand Daltons or more. Small proteins (of less than about 20 amino acids) are usually called peptides or oligopeptides.

Enamel matrix proteins are proteins which normally are present in enamel matrix, i.e. the precursor for enamel (Ten Cate: Oral Histology, 1994; Robinson: Eur. J. Oral Science, January 1998, 106 Suppl. 1:282-91), or proteins which can be obtained by cleavage of such proteins. In general such proteins have a molecular weight below 120,000 daltons and include amelogenins, non-amelogenins, proline-rich non-amelogenins, amelins (ameloblastin, sheathlin), tuftelins, dentinsialoprotein (DSP) or dentinsialophosphoprotein (DSPP).

Examples of proteins for use according to the invention are amelogenins, proline-rich non-amelogenins, tuftelin, tuft proteins, serum proteins, salivary proteins, amelin, ameloblastin, sheathlin, and derivatives thereof, and mixtures thereof. A preparation containing an active enamel substance for use according to the invention may also contain at least two of the aforementioned proteinaceous substances. A commercial product comprising amelogenins is marketed as EMDOGAIN® (Biora AB) and comprises about 30 mg/ml active enamel substance in propylene-glycol- alginate (PGA).

In general, the major proteins of an enamel matrix are known as amelogenins. They constitute about 90% w/w of the matrix proteins. The remaining 10% w/w includes proline-rich non-amelogenins, tuftelin, tuft proteins, serum proteins and at least one salivary protein; however, other proteins may also be present such as, e.g., amelin (ameloblastin, sheathlin) which have been identified in association with enamel matrix. Furthermore, the various proteins may be synthesised and/or processed in several different sizes (i.e. different molecular weights). Thus, the dominating proteins in enamel matrix, amelogenins, have been found to exist in several different sizes which together form supramolecular aggregates. They are markedly hydrophobic substances which under physiologically conditions form aggregates. They may carry or be carriers for other proteins or peptides.

Other protein substances are also contemplated to be suitable for use according to the present invention. Examples include proteins such as proline-rich proteins and polyproline. Other examples of substances which are contemplated to be suitable for use according to the present invention are aggregates of such proteins, of enamel matrix derivatives and/or of enamel matrix proteins as well as metabolites of enamel matrix, enamel matrix derivatives and enamel matrix proteins. The metabolites may be of any size ranging from the size of proteins to that of short peptides.

As mentioned above, the proteins, polypeptides or peptides for use according to the invention typically have a molecular weight of at the most about 120 kDa such as, e.g., at the most 100 kDa, 90 kDa, 80 kDa, 70 kDa or 60 kDa as determined by SDS Page electrophoresis.

The proteins for use according to the invention are normally presented in the form of a preparation, wherein the protein content of the active enamel substance in the preparation is in a range of from about 0.05% w/w to 100% w/w such as, e.g., about 5-99% w/w, about 10-95% w/w, about 15-90% w/w, about 20-90% w/w, about 30-90% w/w, about 40-85% w/w, about 50-80% w/w, about 60-70% w/w, about 70-90% w/w, or about 80-90% w/w.

A preparation of an active enamel substance for use according to the invention may also contain a mixture of active enamel substances with different molecular weights.

The proteins of an enamel matrix can be divided into a high molecular weight part and a low molecular weight part, and it has been found that a well-defined fraction of enamel matrix proteins possesses valuable properties with respect to treatment of periodontal defects (i.e. periodontal wounds). This fraction contains acetic acid extractable proteins generally referred to as amelogenins and constitutes the low molecular weight part of an enamel matrix (cf. EP-B-0 337 967 and EP-B-0 263 086).

As discussed above the low molecular weight part of an enamel matrix has a suitable activity for inducing binding between hard tissues in periodontal defects. In the present context, however, the active proteins are not restricted to the low molecular weight part of an enamel matrix. At present, preferred proteins include enamel matrix proteins such as amelogenin, amelin, tuftelin, DSP, etc. with molecular weights (as measured in vitro with SDS-PAGE) below about 60,000 daltons.

Accordingly, it is contemplated that the active enamel substance for use according to the invention has a molecular weight of up to about 40,000 such as, e.g. a molecular weight of between about 5,000 and about 25,000.

Within the scope of the present invention is also the use according to the invention of peptides as described in WO 97/02730, i.e. peptides which comprise at least one sequence element selected from the group consisting of the tetrapeptides DGEA (Asp-Gly-Glu-Ala), VTKG (Val-Thr-Lys-Gly), EKGE (Glu-Lys-Gly-Glu) and DKGE (Asp-Lys-Gly-Glu) and which further comprise an amino acid sequence from which a consecutive string of 20 amino acids is identical to a degree of at least 80% with a string of amino acids having the same length selected from the group consisting of the amino acid sequence shown in SEQ ID NO:1 and a sequence consisting of amino acids 1 to 103 of SEQ ID NO:1 and amino acids 6 to 324 of SEQ ID NO:2.

By the term sequence "identity" is meant the identity in sequence of amino acids in the match with respect to identity and position of the amino acids of the peptides. A gap is counted as non-identity for one or more amino acids as appropriate.

Such peptides may comprise from 6 to 300 amino adds, e.g. at least 20 amino acids, at least 30 amino acids, such as at least 60 amino acids, at least 90 amino acids, at least 120 amino acids, at least 150 amino adds or at least 200 amino acids.

A method for the isolation of enamel matrix proteins involves extraction of the proteins and removal of calcium and phosphate ions from solubilised hydroxyapatite by a suitable method, e.g. gel filtration, dialysis or ultrafiltration (see e.g. Janson, J-C & Rydén, L. (Eds.), Protein purification, VCH Publishers 1989 and Harris, ELV & Angal, S., Protein purification methods—A practical approach, IRL Press, Oxford 1990).

A typical lyophilised protein preparation may mainly or exclusively up to 70-90% contain amelogenins with a molecular weight (MW) between 40,000 and 5,000 daltons, the 10-30% being made up of smaller peptides, salts and residual water. The main protein bands are at 20 kDa, 12-14 kDa and around 5 kDa as determined by SDS-PAGE.

By separating the proteins, e.g. by precipitation, ion-exchange chromatography, preparative electrophoresis, gel permeation chromatography, reversed phase chromatography or affinity chromatography, the different molecular weight amelogenins can be purified.

The combination of molecular weight amelogenins may be varied, from a dominating 20 kDa compound to an aggregate of amelogenins with many different molecular weights between 40 and 5 kDa, and to a dominating 5 kDa compound. Other enamel matrix proteins such as amelin, tuftelin or proteolytic enzymes normally found in enamel matrix, can be added and carried by the amelogenin aggregate.

As an alternative source of the enamel matrix derivatives or proteins one may also use generally applicable synthetic routes well-known for a person skilled in the art or use cultivated cells or bacteria modified by recombinant DNA-techniques (see, e.g., Sambrook, J. et al.: Molecular Cloning, Cold Spring Harbor Laboratory Press, 1989).

Physico-chemical Properties of Enamel Matrix, Enamel Matrix Derivatives and Enamel Matrix Proteins In general the enamel matrix, enamel matrix derivatives and enamel matrix proteins are hydrophobic substances, i.e. less soluble in water especially at increased temperatures. In general, these proteins are soluble at non-physiological pH values and at a low temperature such as about 4-20° C., while they will aggregate and precipitate at body temperature (35-37° C.) and neutral pH.

The enamel matrix, enamel matrix derivatives and/or enamel matrix proteins for use according to the invention also include an active enamel substance, wherein at least a part of the active enamel substance is in the form of aggregates or after application in vivo is capable of forming aggregates. The particle size of the aggregates is in a range of from about 20 nm to about 1 μm.

The enamel matrix, enamel matrix derivatives and enamel matrix proteins have also been observed (by the present inventors) to posses bioadhesive properties, i.e. they have an ability to adhere firmly to tissue surfaces. These properties are most valuable in connection with endodontic treatment not least because they ensure a fast and intimate contact between the enamel matrix proteins and the dentin-producing odontoblasts so as to facilitate the process of dental root regeneration.

Theories with Respect to Mechanism of Action

Enamel matrix is an example of an extracellular protein matrix which adheres to mineral surfaces as well as to proteinaceous surfaces. At physiological pH and temperature the amelogenins present in enamel matrix form an insoluble supra-molecular aggregate (Fincham et al. in J. Struct. Biol. 1994 March-April; 112(2):103-9 and in J. Struct. Biol. 1995 July-August; 115(1):50-9), which is gradually degraded by proteolytic enzymes (occurs both in vivo and in vitro provided that the proteases have not been subjected to inactivation).

The recent observation that enamel matrix is formed and temporarily present during root and root cementum formation can explain how application of enamel matrix, enamel matrix derivatives and/or enamel matrix proteins promotes the regeneration of periodontal tissue. However, the observation underlying the present invention that enamel matrix, enamel matrix derivatives and/or enamel matrix proteins also exert a positive effect on formation or regeneration of endodontic tissue, i.e. dental pulp tissue, is very surprising.

In one embodiment of the present invention, glass-ionomer cement is used for cavity restoration after the pulp capping procedure, and no adhesive resin system. EMD is herein used to induce pulpal wound healing and rapid dentin formation, meaning that EMD treated teeth develop features of classic wound healing, i.e. a superficial layer or scab, consisting of extracellular matrix proteins and necrotic cell remnants, overlaying a zone of chronic inflammatory cell infiltrate. EMD in this embodiment further promotes the formation of a bridge of new dentin, sealing off the wound from the healthy pulp tissue, wherein the pulp tissue subjacent to the new dentin is free of signs of inflammation. Moreover, an intact layer of functional odontoblasts is formed, abutting on the newly formed dentin.

These findings suggest that EMD has the potential to rapidly induce new dentin formation when applied onto a coronal pulpal wound without affecting the more apical part of the pulp tissue. The isolation of the wounded tissue from the remaining healthy pulp tissue can be regarded as an ideal form of pulp healing for clinical use. The effect of EMD resembles the effects of a scab during dermal wound healing, promoting the classical wound healing cascade and the subsequent tissue regeneration or repair.

It has previously been shown in clinical experiments that the protein layer formed by EMD is retained on the wound surface for at least a week after application (Gestrelius S, Andersson C, Johansson AC, Persson E, Brodin A, Rydhag L, Hammarstrom L (1997). Formulation of enamel matrix derivative for surface coating. Kinetics and cell colonization. J Clin Periodontol:678-684). Recently, it is also reported that growth of gram-negative bacteria is inhibited by the presence of EMD. Thus, EMD components may not only act as a signal for mesenchymal cell differentiation and maturation in the wounded pulp tissue, but also by forming a stable extracellular matrix that acts as a protective crust covering the wound as a scab.

The mechanism(s) underlying the induction of new dentin formation by EMD is still not known in detail. However, recent laboratory findings suggest that that EMD induces an intracellular cyclic-AMP signal that triggers autocrine growth expression from fibroblast cells in a well-orchestrated cascade (Lyngstadaas S P, Lundberg E, Ekdahl H, Andersson C and Gestrelius S (2000). Autocrine growth factors in human periodontal ligament cells cultured on enamel matrix derivative. J Clin Periodontol (in press)). Following the release of growth factors EMD exposed cells then proliferate and mature into extracellular matrix secreting cells. Similar mechanisms may also be at play when the pulpal wound is healing in presence of EMD.

In one embodiment of the present invention, EMD therefore at least provides a protective environment favorable for healing of pulpal wounds. However, the large amount of rapidly forming dentin delineated by new functional odontoblasts suggest that EMD acts more directly by inducing mesenchymal cell differentiation and/or maturation of odontoblast precursor cells residing in the pulp.

A preparation of the active enamel substance is normally formulated as a pharmaceutical composition. Such a composition may of course consist of the proteinaceous preparation or it may further comprise a pharmaceutically acceptable diluent or excipient. The diluent may typically be water in which the active enamel substance is dissolved before application to endodontic tissue.

Pharmaceutical Compositions

In the following examples of suitable compositions containing the active enamel substance are given.

For the administration to an individual (an animal or a human) the enamel matrix, enamel matrix derivatives and/or enamel matrix proteins (in the following also denoted "active enamel substance") and/or a preparation thereof are preferably formulated into a pharmaceutical composition containing the active enamel substance and, optionally, one or more pharmaceutically acceptable excipients.

The compositions may be in form of, e.g., solid, semi-solid or liquid compositions such as, e.g., powders, granules, granulates, capsules, agarose or chitosan beads, tablets, pellets, microcapsules, microspheres, nanoparticles, or freeze-dried powders, granules, granulates or pellets, gels, hydrogels, pastes, solutions, dispersions, suspensions, emulsions, mixtures, kits containing e.g. two separate containers, wherein the first one of the containers contains the active enamel substance optionally admixed with other active drug substance(s) and/or pharmaceutically acceptable excipients and the second container containing a suitable medium intended to be added to the first container before use in order to obtain a ready-to-use composition.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988.

Apart from the active enamel substance, a pharmaceutical composition for use according to the invention may comprise pharmaceutically acceptable excipients.

A pharmaceutically acceptable excipient is a substance which is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients.

The choice of pharmaceutically acceptable excipient(s) in a composition for use according to the invention and the optimum concentration thereof cannot generally be predicted and must be determined on the basis of an experimental evaluation of the final composition. However, a person skilled in the art of pharmaceutical formulation can find guidance in e.g., "Remington's Pharmaceutical Sciences", 18th Edition, Mack Publishing Company, Easton, 1990.

The pharmaceutically acceptable excipients may include solvents, buffering agents, preservatives, chelating agents, antioxidants, stabilisers, suspending agents and gel-forming agents.

Examples of solvents are e.g. water, alcohols, or other hydrophilic or etheric solvents such as weak acids with a pH of about 5.5-6.0 facilitating the subsequent application of filling materials in the tooth.

Examples of buffering agents are e.g. citric acid, acetic acid, tartaric acid, lactic acid, hydrogenphosphoric acid, diethylamine etc.

Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, benzalconium chloride, and benzylalcohol, or mixtures of preservatives.

Examples of antioxidants are butylated hydroxy anisole (BHA), ascorbic acid and derivatives thereof, tocopherol and derivatives thereof, cysteine, and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, microcrystalline cellulose (e.g. Avicel® RC 591), carragheenan, acacia gum, arabic gum, tragacanth, and mixtures thereof.

Examples of gel bases or viscosity-increasing agents are liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates, and alginates including propylene glycol alginate.

Examples of powder components are: alginate, collagen or lactose. Normally, powders intended for application on dental pulps must be sterile and the particles present must be micronized.

Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

Suitable compositions for use according to the invention may also be presented in the form of suspensions, emulsions or dispersions. Such compositions contains the active enamel substance in admixture with a dispersing or wetting agent, suspending agent, and/or one or more preservatives and other pharmaceutically acceptable excipients. Suitable dispersing or wetting agents are, for example, naturally occurring phosphatides, e.g., lecithin, or soybean lecithin; condensation products of ethylene oxide with e.g. a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate, etc.

Dosages of Enamel Matrix, Enamel Matrix Derivatives and Enamel Matrix Proteins

In a pharmaceutical composition for use according to the invention, an active enamel substance is generally present in a concentration ranging from about 0.01% to about 99.9% w/w. The amount of composition applied will normally result in an amount of total protein per $cm^2$ area of dental pulp corresponding to from about 0.005 $mg/mm^2$ to about 5 $mg/mm^2$ such as from about 0.01 $mg/mm^2$ to about 3 $mg/mm^2$.

In those cases where the active enamel substance is administered in the form of a liquid composition, the concentration of the active enamel substance in the composition is in a range corresponding to from about 0.01 to about 50 mg/ml, e.g. from about 0.1 to about 30 mg/ml. Higher concentrations are in some cases desirable and can also be obtained such as a concentration of at least about 100 mg/ml. Defect areas in dental pulp in humans typically have a size of about 5-10×2-4×5-10 mm corresponding to about 200 µl and normally at the most about 0.5-1 ml such as about 0.2-0.3 ml per tooth is applied of a composition having a concentration of about 1-40 mg total protein/ml such as, e.g., 5-30 mg/ml is applied. 0.2-0.3 mg/ml corresponds to about 6 mg protein per 25-100 $mm^2$ or about 0.1 $mg/mm^2$ if calculated only on root surface. Normally an excessive volume is applied to cover the affected surfaces adequately. Even a multilayer would only require a small fraction of the above-mentioned amounts.

The present invention is further described in the following examples which are not in any way intended to limit the scope of the invention as claimed.

Figure Legends

BRIEF DESCRIPTION OF THE DRAWINGS

FIG. 1 shows micrograph showing premolar teeth two weeks after treatment with EMD. The pulp wound has features of a classic active wound, i.e. a necrotic superficial layer overlaying a narrow zone of chronic inflammatory cell infiltrate. The new dentin-like tissue is formed at the border between the wound tissue and the healthy subjacent pulp tissue. Sections stained with H&E.

Shows micrograph showing premolar teeth two weeks after treatment with Ca(OH).sub.2. Normal appearing pulp tissue without inflammatory cells can be observed adjacent to the pulpal wound, resembling an inactive wound typical for a chemical bum. No new dentin or odontoblasts were observed in or close to the wound in these teeth. Sections stained with H&E.

FIG. 3

Showing premolar teeth four weeks after treatment with EMD. The pulp wound now shows features of a classic wound healing, i.e. a superficial layer or scab, consisting of extracellular matrix proteins and cell remnants, overlaying a zone of chronic inflammatory cell infiltrate. Subjacent to the healing wound a bridge of new dentin-like tissue is forming, sealing off the wound from the healthy pulp. Sections stained with H&E.

FIG. 4

Figure 3:
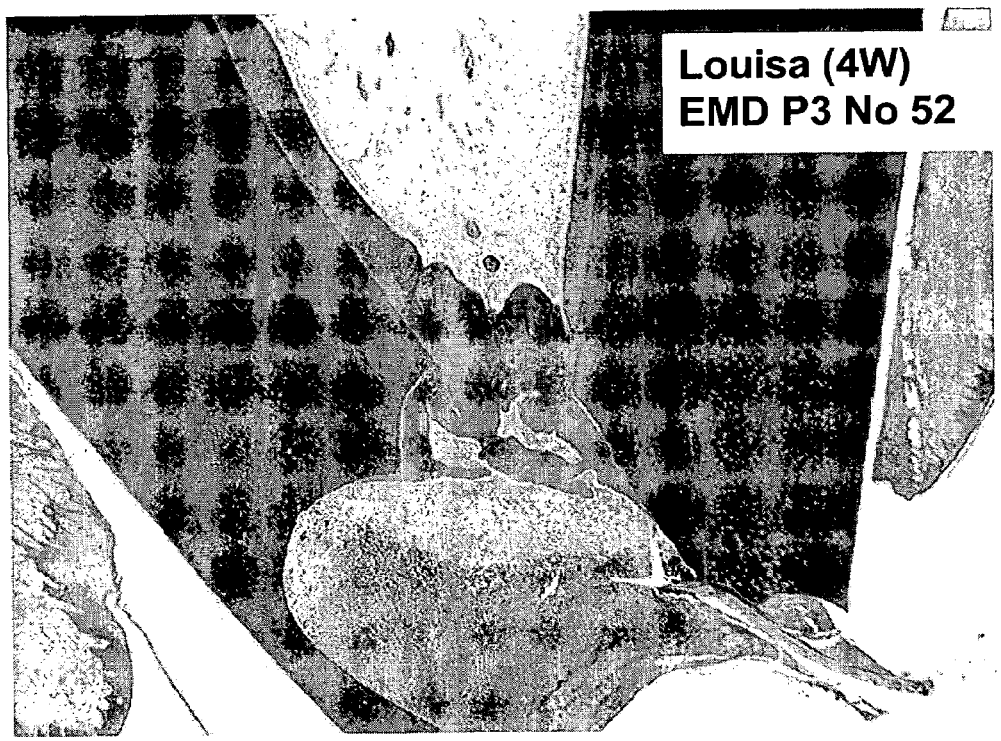

Shows a higher magnification of FIG. 3, the new hard tissue is bordered with odontoblast-like cells and tissue subjacent to the forming bridge is healthy and free of inflammatory cells. Sections stained with H&E.

FIG. 5

Showing premolar teeth four weeks after treatment with $Ca(OH)_2$. Normal appearing pulp tissue without inflammatory cells can be observed adjacent to the inactive pulpal wound. A small amount of new dentin is formed along the preexisting dentin walls adjacent to the wound. Sections stained with H&E.

FIG. 6

Showing premolar teeth four weeks after treatment with $Ca(OH)_2$. Normal appearing pulp tissue without inflammatory cells can be observed adjacent to the inactive pulpal wound. A small amount of new dentin is formed along the preexisting dentin walls adjacent to the wound. Sections stained with H&E.

FIG. 7

Figure 7A:
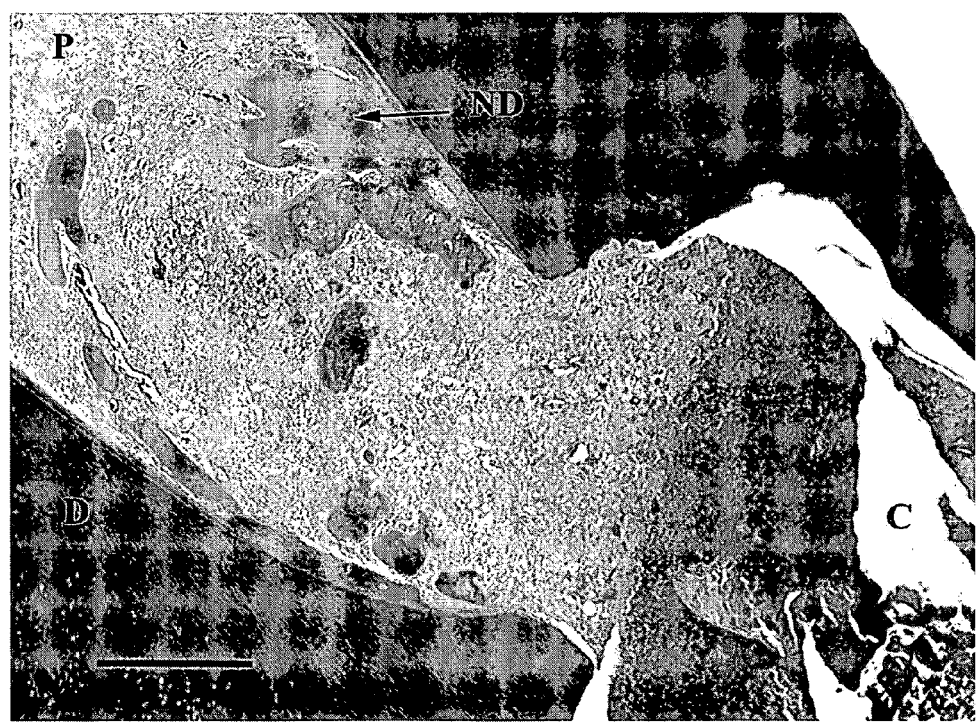

FIG. 7a shows tooth treated with EMD. The pulp wound shows features of a classic active wound, i.e. a necrotic superficial layer overlaying a narrow zone of chronic inflammatory cell infiltrate. The new dentin (ND) is formed at the border between the wound tissue and the healthy subjacent pulp tissue.

Figure 7B:
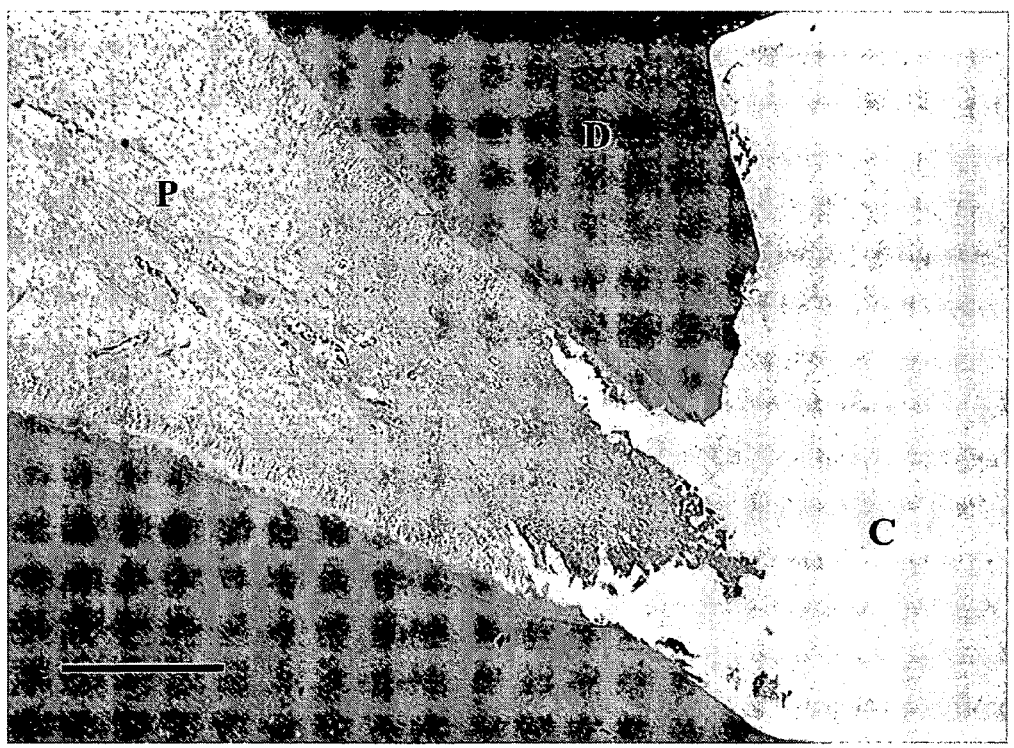

FIG. 7b shows tooth treated with Ca(OH) Normal appearing pulp tissue without inflammatory cells can be observed adjacent to the inactive pulpal wound, resembling an inactive wound typical for a chemical burn. No new dentin or odontoblasts were observed in or close to the wound in these teeth.

C is experimental cavity. D is dentin, ND is newly formed dentin, and P is pulp tissue. Sections stained with H&E, scale bar is 1 mm.

FIG. 8

Micrographs showing premolar teeth four weeks after treatment with EMD or $Ca(OH)_2$.

Figure 8A:
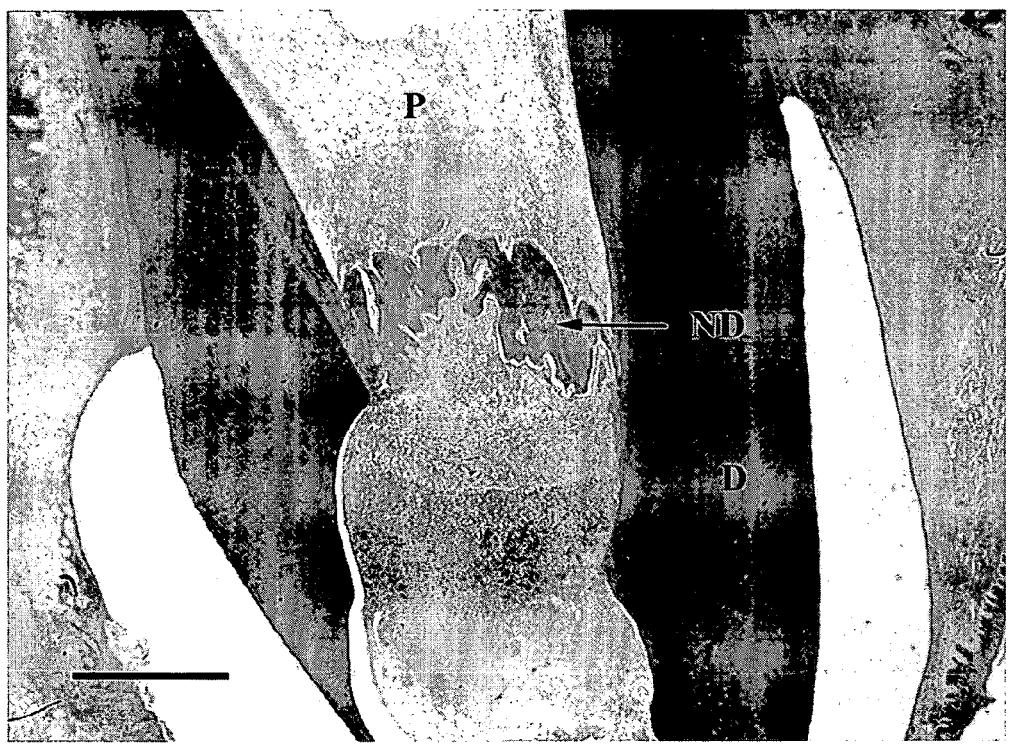

FIG. 8a shows tooth treated with EMD. The pulp wound now shows features of a classic wound healing, i.e. a superficial layer or scab, consisting of extracellular matrix proteins and cell remnants, overlaying a zone of chronic inflammatory cell infiltrate. Subjacent to the healing wound a bridge of new dentin (ND) is forming, sealing off the wound from the healthy pulp tissue.

Figure 8B:
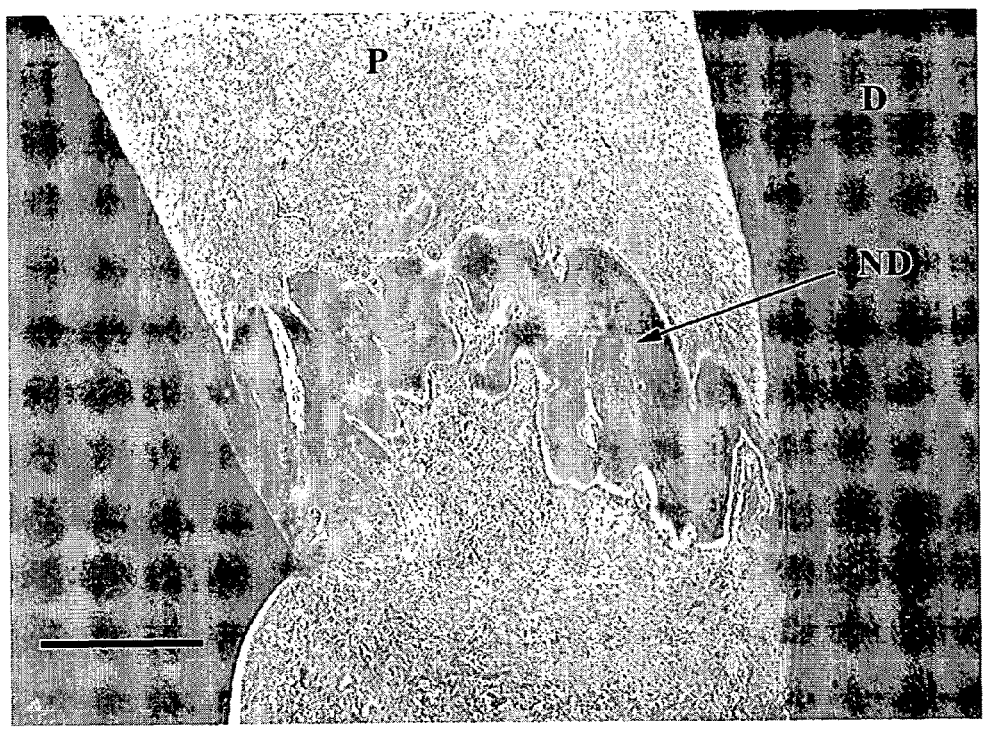

FIG. 8b Shows a higher magnification of 8a), the new dentin is bordered with normal appearing odontoblast and tissue subjacent to the forming dentin bridge is healthy and free of inflammatory cells.

Figure 8C:
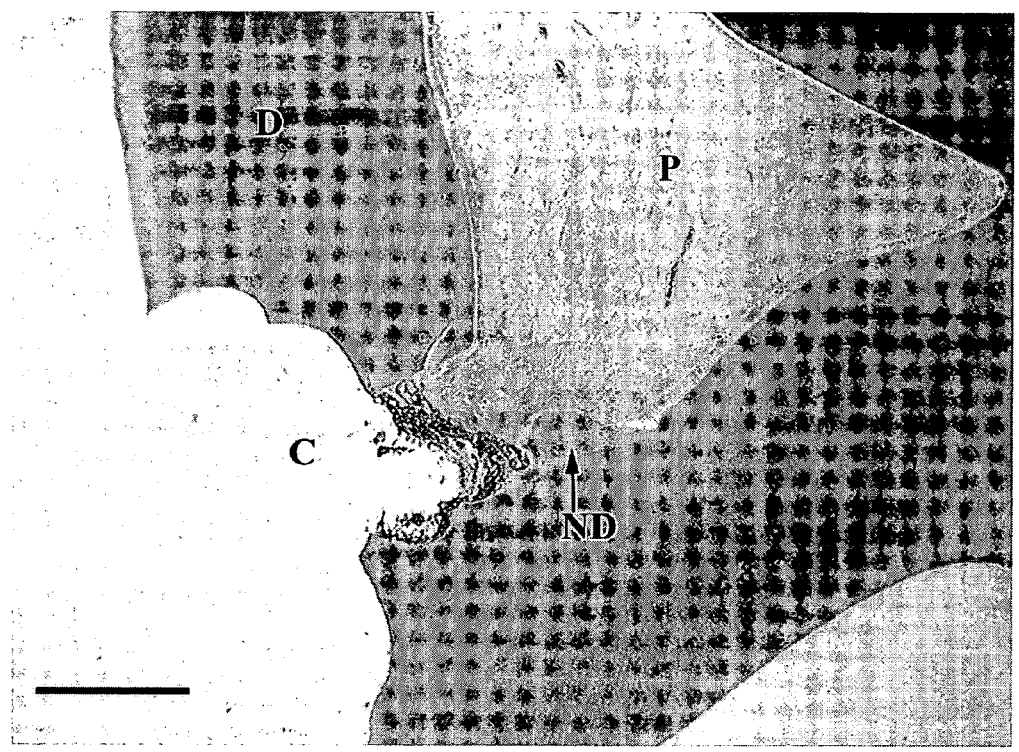

FIG. 8c shows tooth treated with Ca(OH) Normal appearing pulp tissue without inflammatory cells can be observed adjacent to the inactive pulpal wound. A small amount of new dentin is formed along the dentin walls adjacent to the wound. Occasionally, small islands of irregular dentin could be observed in the surrounding pulp tissue at some distance from the wound site.

C is experimental cavity. D is dentin, ND is newly formed dentin, and P is pulp tissue. Sections stained with H&E, scale bar is 1 mm (a and c) or 0.5 mm (b).

FIG. 9

Chart expressing the total amount of new dentin formed after two and four weeks in experimental teeth following EMD or $Ca(OH)_2$ application and cavity sealing. The amount of new dentin is presented in $mm^2$, measured by histometry in serial sections. At both stages, the amount of new dentin formed in EMD treated teeth was significantly higher than in the $Ca(OH)_2$ treated teeth. n=11 at all time-points. Error bars give ±SD. p<0,001 for both series.

FIG. 10

Micrographs showing incisor teeth 3, 4 and 8 weeks after treatment with EMD (FIGS. 10-a, b, c) or $Ca(OH)_2$ (FIGS. 10-d, e, f). a) Micrograph of amputated pulp treated with EMD after 3 weeks. The pulp wound has features of a necrotic superficial "scab" layer overlaying a zone of moderate inflammatory cell infiltrate. b) Micrograph of amputated pulp treated with EMD after 4 weeks. Moderate amounts of a new dentine-like tissue bridge the full width of the cavity at the interface between the wounded and the unharmed pulp tissue. c) Micrograph of amputated pulp treated with EMD after 8 weeks. The dentine bridge formation can be observed in the vital pulp at some distance from the amputated site, sealing off the wounded pulp tissue and scab with inflammatory cells (IC). d) Micrograph of amputated pulp treated with $Ca(OH)_2$ after 3 weeks. There is liquefaction necrosis close to the calcium hydroxide paste (CA). A zone of newly formed pre-dentine is observed forming onto and along the circumpulpal dentine wall subjacent to the amputation site. e) Micrograph of amputated pulp treated with $Ca(OH)_2$ after 4 weeks. Newly formed secondary dentine formed directly onto and along the pre-existing dentine walls leading to a significant narrowing of the pulp chamber. f) Micrograph of amputated pulp treated with $Ca(OH)_2$ after 8 weeks. The resulting dentine bridge is significantly thinner layer than the bridges formed in the EMD treated teeth.

D is dentine, P is pulp tissue, IC is inflammatory cells and CA is calcium hydroxide paste (Original magnification×20. Section stained with H & E, scale bar is 1 mm).

FIG. 11

Figure 10A:
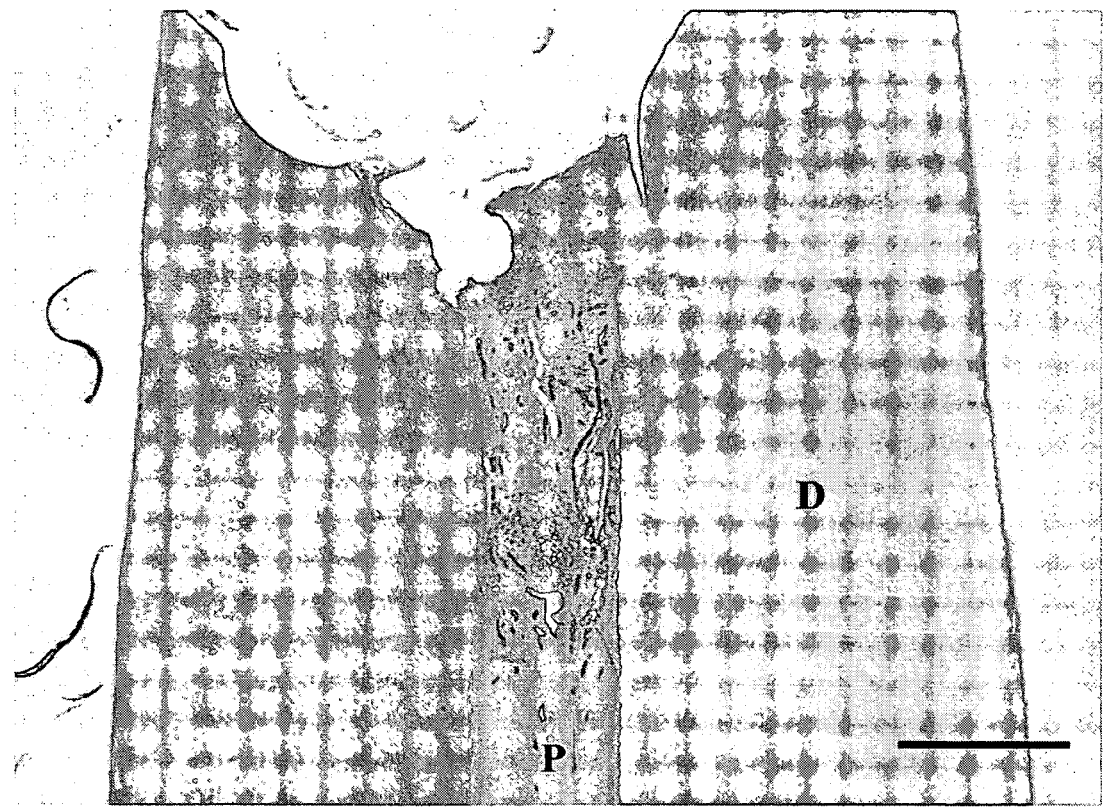
Figure 10B:
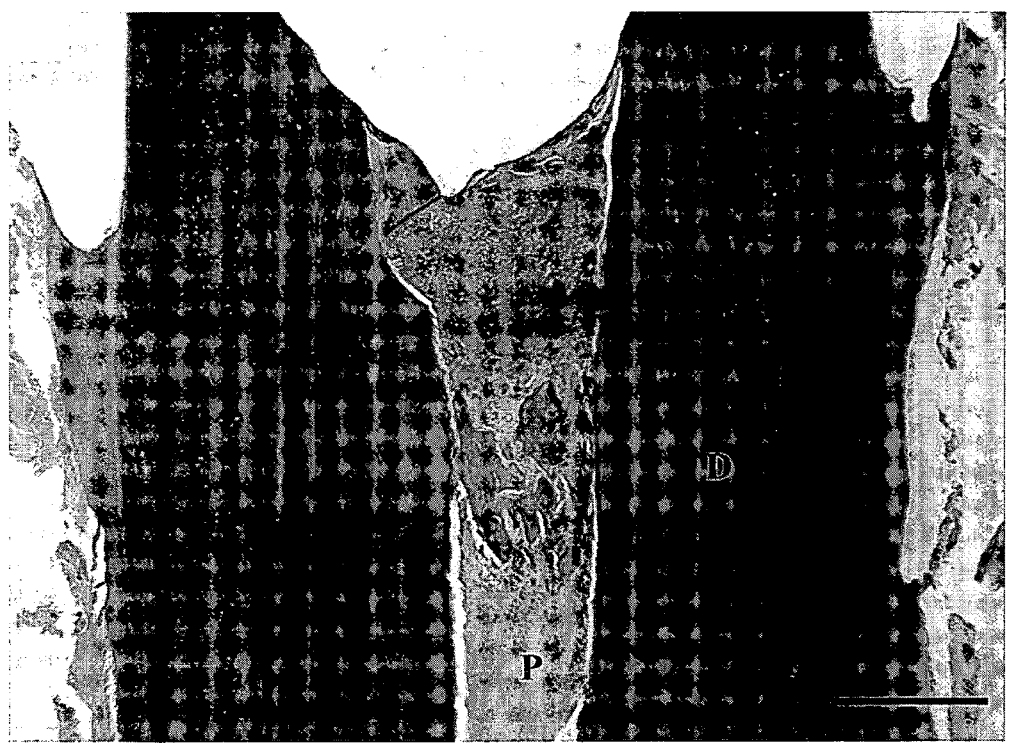
Figure 10C:
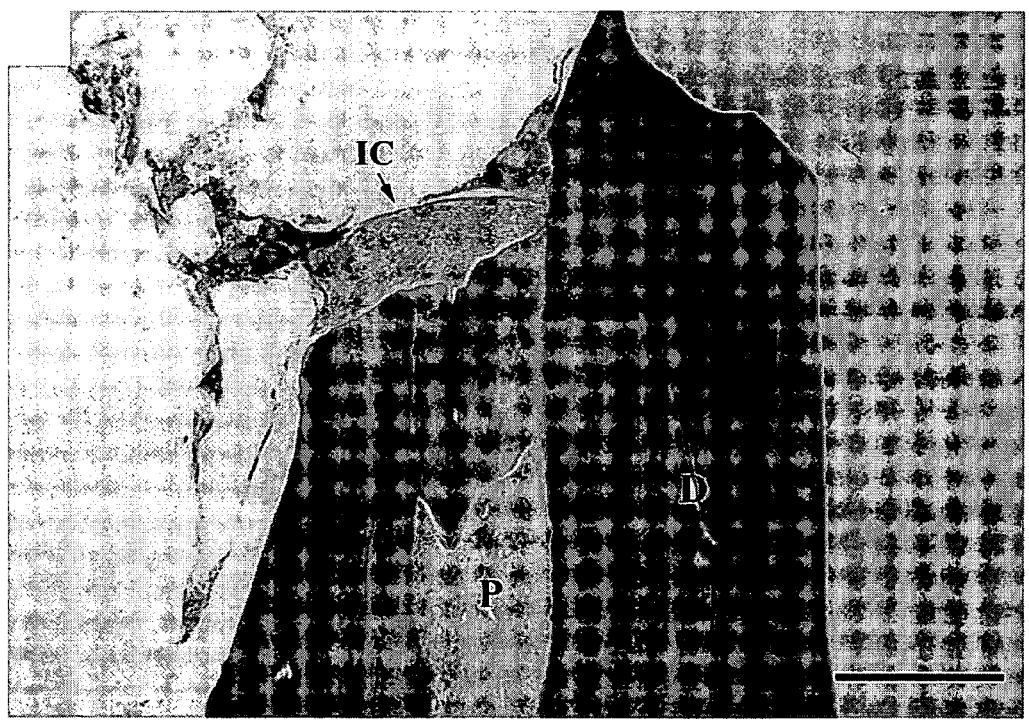
Figure 10D:
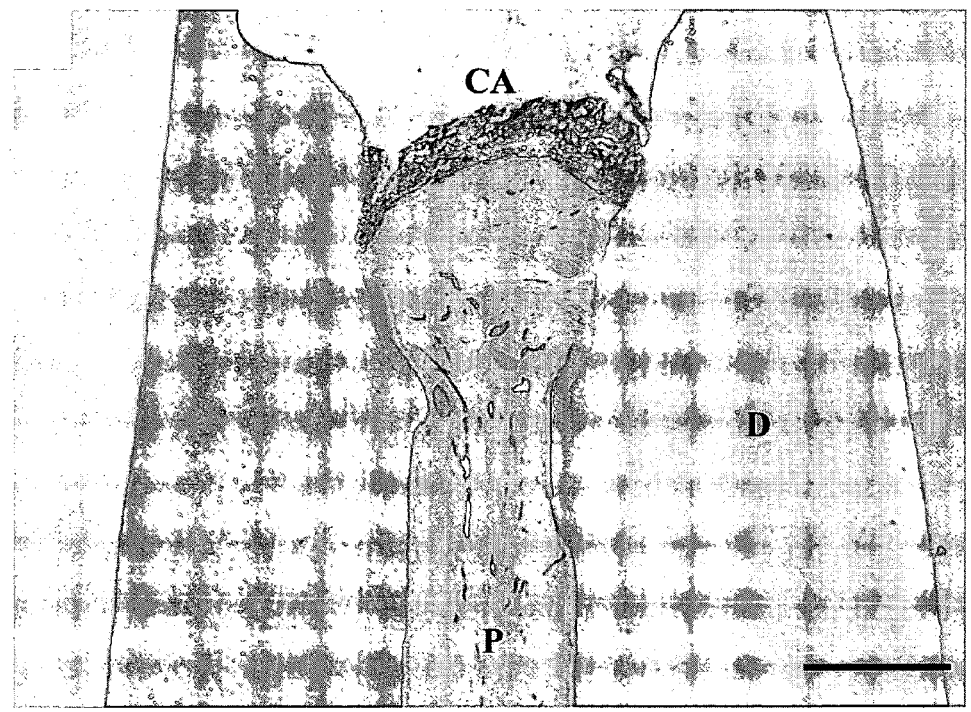

Higher magnification of FIG. 10a and FIG. 10d.

a) In EMD treated teeth a marked increase in angiogenesis is evident in the deeper part of the pulp tissue subjacent to the application sites.

b) New blood vessels situated close to the pre-existing odontoblasts indicate an increased activity in these cells.

D is dentine, P is pulp tissue and CA is calcium hydroxide paste (Original magnification×40. Section stained with H & E, scale bar is 0.5 mm).

FIG. 12

Figure 10E:
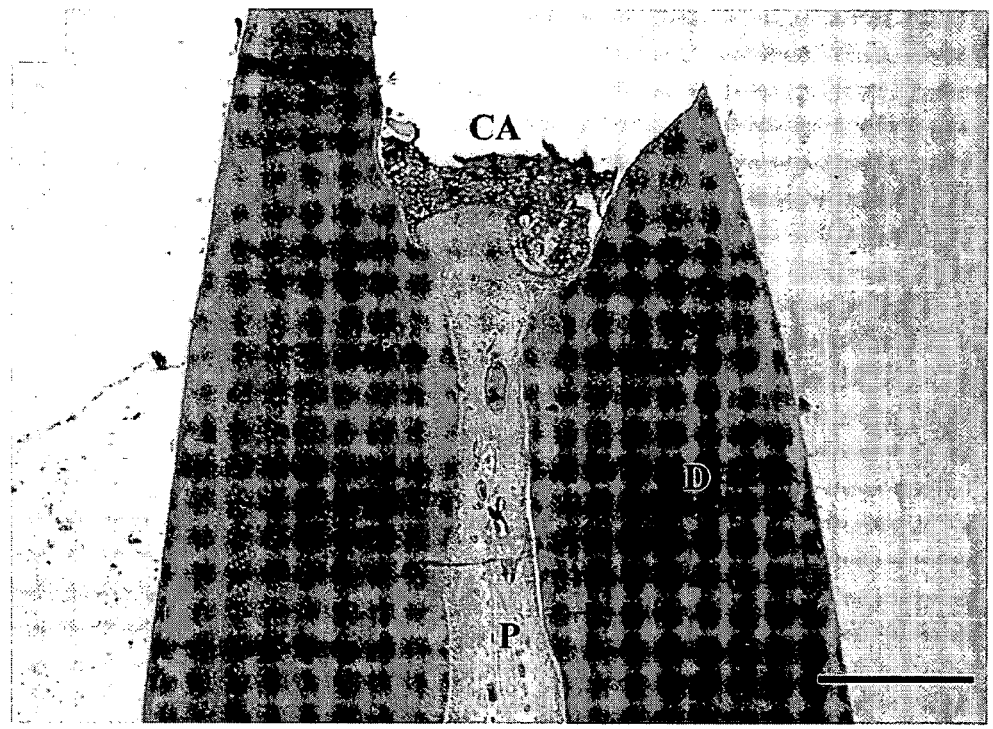

Higher magnification of FIG. 10b and FIG. 10e.

a) In EMD treated teeth a web of new hard-tissue islets in dose contact with newly formed odontoblast-like cells surrounded the new dentine bridge on the apical side.

b) In control teeth new hard tissue resembles secondary dentine that forms only onto the root canal wall and no bridging was observed at this stage.

D is dentine, P is pulp tissue and CA is calcium hydroxide paste (Original magnification×40. Section stained with H & E, scale bar is 0.5 mm).

FIG. 13

Figure 10F:
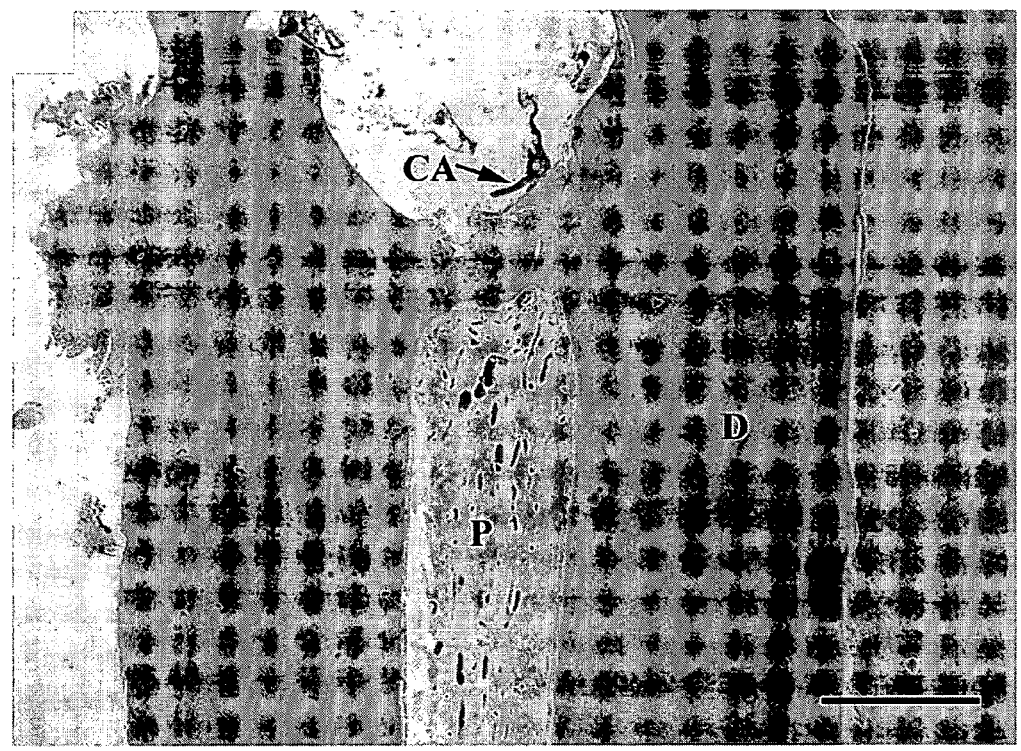

Higher magnification of FIG. 10c and FIG. 10f.

a) In EMD treated teeth the dentine bridges are bordered with odontoblast-like cells and the tissue subjacent to the bridge is healthy and free of inflammatory cells.

b) In control teeth the formed dentine bridge is significantly thinner than in EMD treated teeth.

D is dentine, P is pulp tissue and CA is calcium hydroxide paste (Original magnification×40. Section stained with H & E, scale bar is 0.5 mm).

EXPERIMENTAL SECTION

Example 1

Six adult (18 months of age or older) Göttingen minipigs (available from Møllegård, Denmark) were anesthesized with Dormicum (a general anesthetic available from Roche; Switzerland) and also locally anesthesized by injection of Xylocain and adrenalin. The pulps of permanent maxillary premolars and molars (a total of 36 teeth) were exposed in buccal class V cavities using a sterilised round steel burr (No. 12) with saline spray. The most coronal part of the pulp was then removed to make a pulp wound of with an area of more than 2 square millimeters. The vitality of the pulp was demonstrated by abundant bleeding that was brought under control using sterile cotton pellets. After bleeding had stopped, an enamel matrix derivative (EMD, Emdogain®, available from Biora AB) or Ca(OH)2 paste (Dycal Dentine, available from Dentsply De Trey, Switzerland) as control, were applied directly onto the exposed pulp. The cavities were then sealed with a commercially available glass ionomer filling (GC Fuji II, Fuji Co., Japan) in a procedure mimicking ordinary clinical situations.

Figure 1:
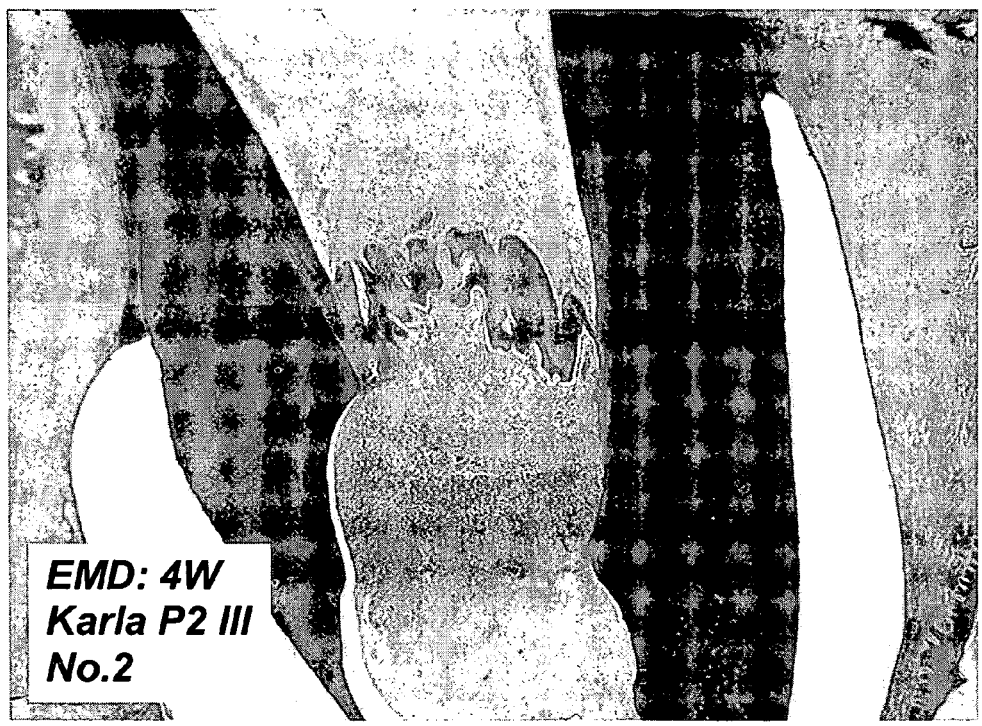
FIG. 1
Figure 2:
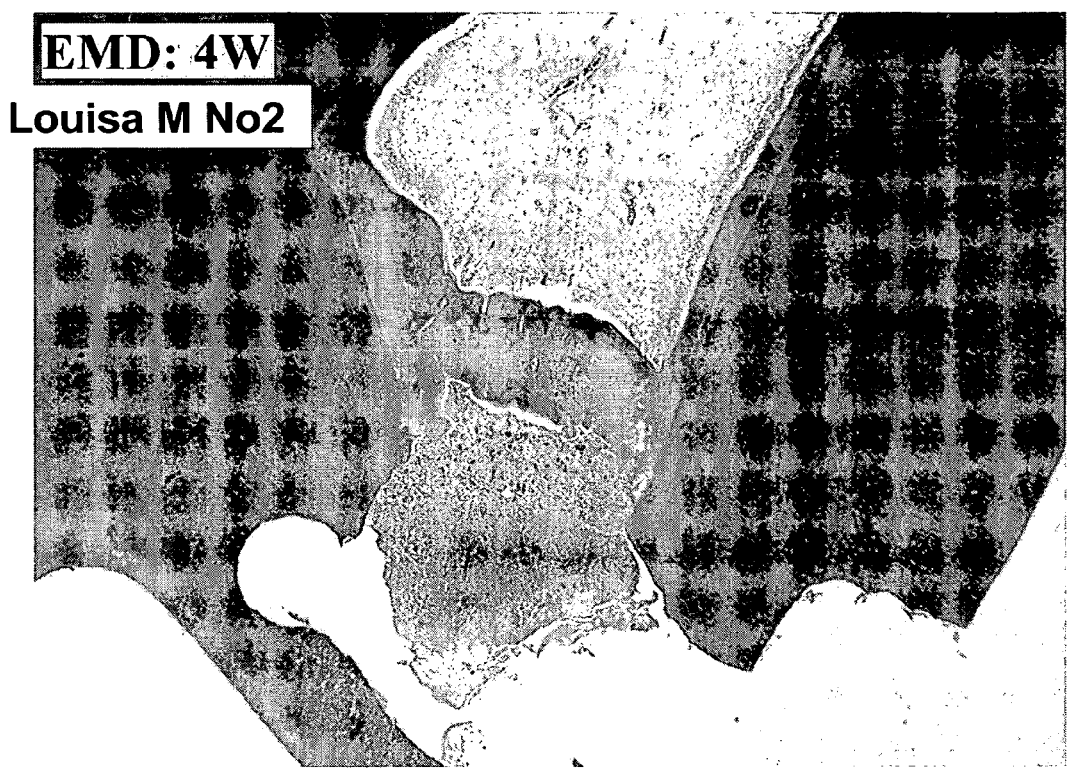
FIG. 2
Figure 4:
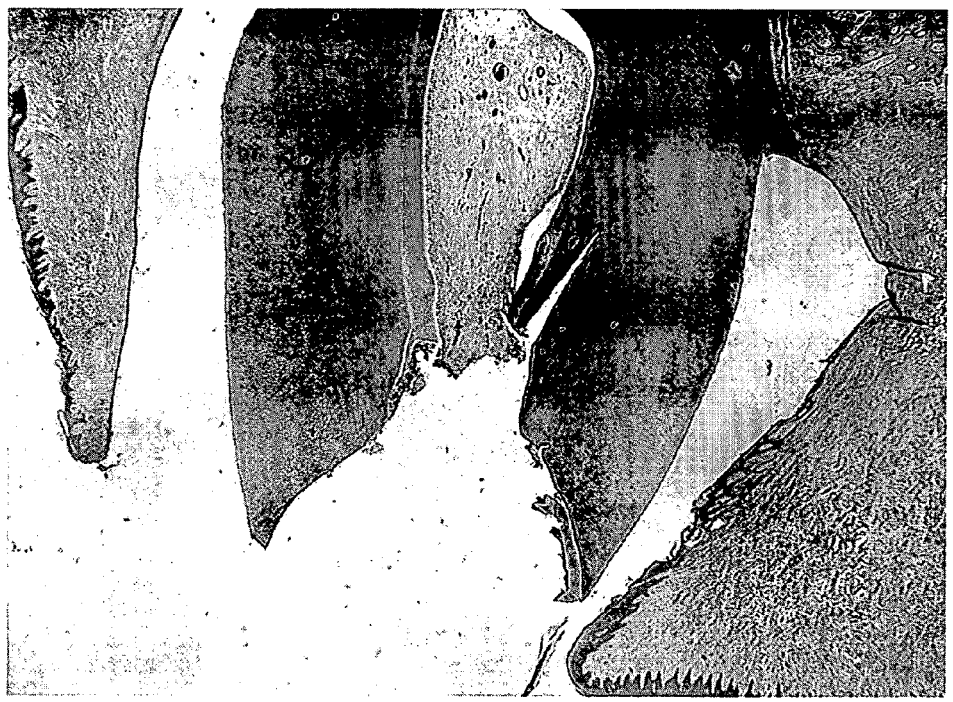
Figure 5:
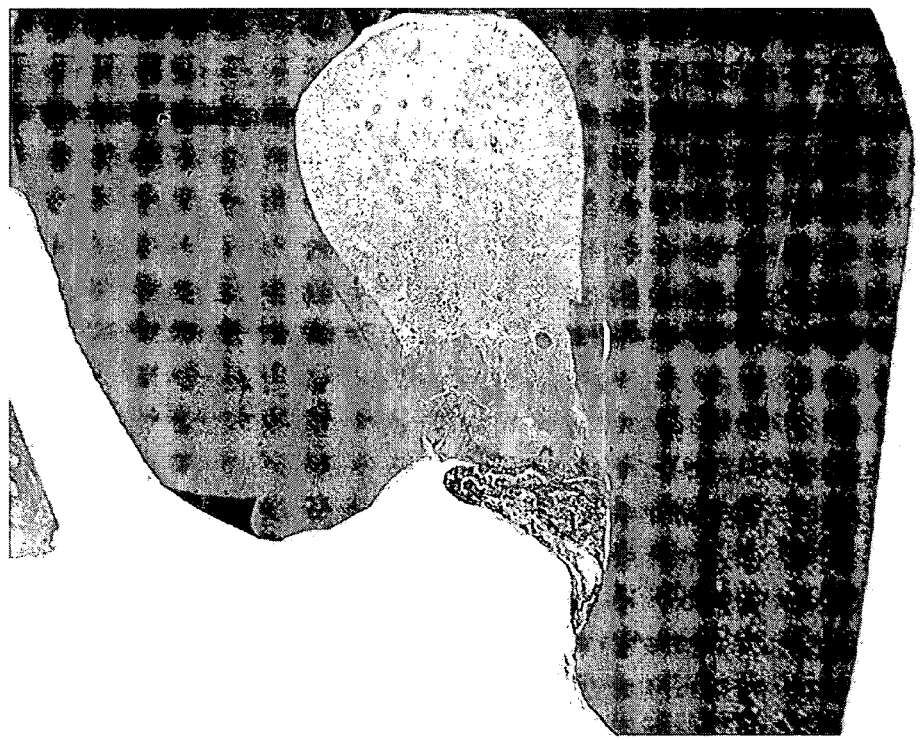
Figure 6:

After two or four weeks, the animals were sacrificed and the experimental teeth were extracted and embedded in paraffin, and histological sections were stained with hematoxylin and eosin. Microscopy of the histological sections revealed a thick dentin-like closure of the pulp chamber adjacent to the filling material after four weeks in the location where EMD had been applied (FIGS. 1-3). In controls without EMD no or only rudimentary dentin formation was observed and none of the control teeth exhibited complete closures of the pulp chamber (FIGS. 4-6).

Example 2

Coronal pulp tissue of permanent maxillary premolars and molars in miniature swine were exposed through buccal class V cavities. The exposed pulp was capped with EMD. Calcium hydroxide paste was used as capping material in contralateral control teeth. After the procedure, cavities were sealed with glass-ionomer cement. At 2 and 4 weeks post surgery, serial sections were prepared and stained with hematoxylin and eosin and analyzed blindly by histometry. In EMD-treated teeth large amounts of newly formed dentin with abutting odontoblast outlined the pulpal wound, isolating the cavity area from the remaining healthy pulp tissue. Inflammatory cells were present in the wound but not subjacent to the newly formed dentin in these teeth. Calcium hydroxide treated control teeth showed only fragmentary new dentin formation. The amount of new dentin in EMD treated teeth was more than twice that of the controls (p<0,001).

Surgical Procedure

A total of 22 teeth from 4 adults miniature swine were used in these experiments. The animals were anaesthetized with an intramuscular injection of 10 ml Ketalar® and 8 ml pentobarbital i.v. The surgical sites were infiltrated with Xylocain® (20 mg/ml) and adrenalin (12.5 µg/ml). Each tooth pulp was exposed trepanation through a 2-mm diameter buccal class V cavity using sterile burs and sterile saline spray. Bleeding was controlled with sterile cotton pellets. The exposed pulp tissue was then capped with EMDOGAIN®(BIORA AB, Malmö, Sweden) or calcium hydroxide (Dycal®: DENTSPLY, Konstanz, Germany), and each cavity was filled with glass-ionomer cement (GC Fuji II®: GC Corporation, Tokyo, Japan).

Histological Examination

At 2 and 4 weeks after surgery, the animals were sacrificed by intra-cordial bolus injection of 50 ml sodium pentobarbital in ethanol. Following euthanasia, all experimental teeth and the adjacent alveolar bone were removed en block and fixed in cold 4% neutral buffered formaldehyde for 24 hours. The specimens were then demineralized in 12.5% EDTA and subsequently embedded in paraffin. After serial sectioning (6 µm) every second section was stained with hematoxylin and eosin. Series of sections containing coronal pulp tissue were then analyzed in a light microscope equipped for histometry (Olympus Microimage®).

Quantitative Analyses of Newly Formed Dentin

The amount of new dentin formed adjacent to the calibrated cavity in each experimental tooth was assessed in the 20 most central sections from each tooth, by measuring the area of new dentin in every second stained section. The apical cut-off distance was set to 3 mm from the bottom of the experimental cavity.

Results

Two weeks after surgery a necrotic layer was observed overlaying a zone of moderately infiltrated with chronic inflammatory cells was observed adjacent to the experimental cavities in EMD treated teeth. Newly formed dentin nodules outlined by a distinct odontoblast layer bordered the wound (FIG. 7a).

In teeth treated with Ca(OH)2 there was no signs of inflammation at this age, and normal appearing connective tissue was demonstrated in close contact with the capping material. However, no odontoblast or new dentin were present adjacent to the experimental cavity in these teeth (FIG. 7b).

Four weeks after surgery a large amount of new dentin, bridging the full width of the cavity, had formed at the interface between the wounded tissue and the vital pulp tissue in the EMD treated teeth. In consequence, the dentine bridge formation was observed in the vital pulp at some distance from the most apical part of the experimental cavity, sealing off the traumatized part of the pulp including the necrotised tissue and the inflammation cells (FIGS. 8a and 8b). The pulp tissue subjacent to the dentin bridge appeared normal and free of inflammation. A distinct layer of functional odontoblast could be observed abutting on the newly formed dentin.

In calcium hydroxide controls, only a small amount of scattered, new dentin was observed in association with the exposed site at four weeks post-surgery, mostly adjacent to the old dentin. In some of these teeth, small amounts of a reactive, irregular, hard-tissue could be demonstrated at the pulpal wound. There were no signs of inflammation in the Ca(OH)2 treated teeth (FIG. 8c).

Figure 9:
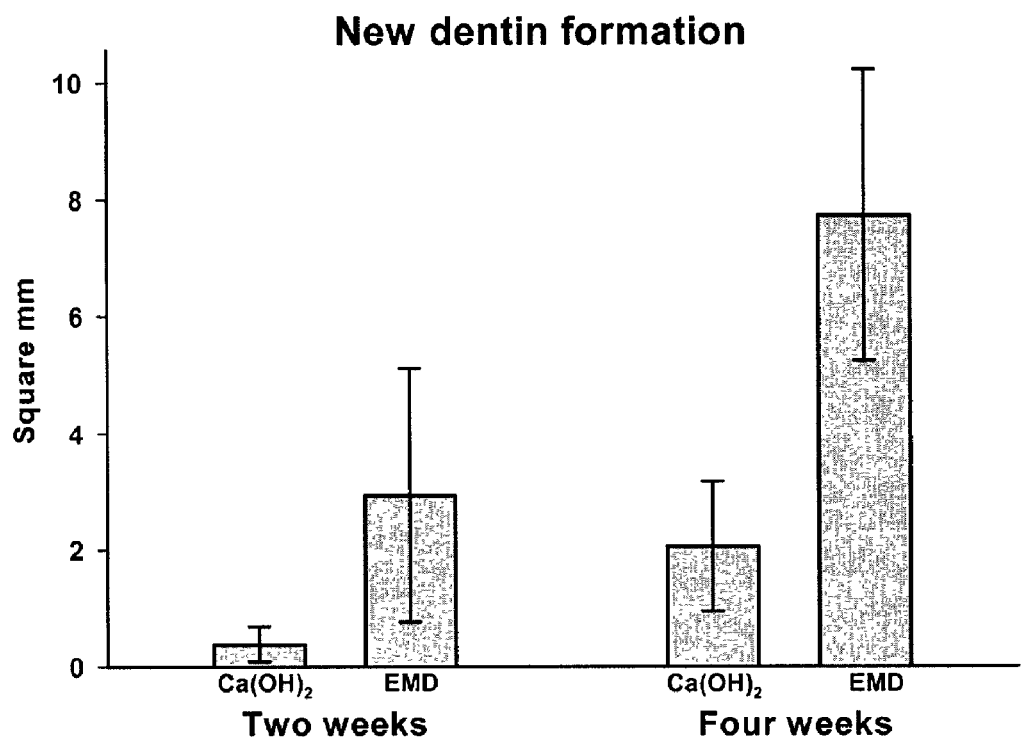

Quantitative analyses of newly formed dentin calculated as the sum of areas covered by new dentin in the five most central sections from each experimental cavity, revealed a significant (p<0,001) increase in dentin formation in EMD treated teeth when compared to Ca(OH)2 treatment (FIG. 9). After both two and four weeks, the amount of dentine in the EMD treated teeth was more than twice that of the controls.

Example 3

This study was designed to examine if enamel matrix derivative (EMD) could induce reparative dentine formation without eliciting adverse side effects in pulpotomized teeth. For this purpose, pulpotomy were performed in 36 lower incisor teeth from 11 adult miniature swine. Following the surgical procedure the exposed pulp tissue was treated with EMD or covered with a calcium hydroxide preparation. Following an observation period of 2, 3, 4 and 8 weeks the experimental teeth were extracted and examined histologically. The results demonstrate that in EMD treated teeth substantial amounts of dentine-like tissue formation consistently led to a complete hard-tissue bridging of the defects. The onset of hard tissue formation could be observed already after two weeks and was located only to the pulpal wound region. Dentine formation, albeit not to the same extent as observed in EMD treated teeth, was also observed in calcium hydroxide treated teeth. However, in these control teeth the new hard tissue formed at the expense of pulp chamber width, causing narrowing of the root canal and subsequent strangulation of the pulp tissue. The total amount of newly formed mineralized tissue in the EMD treated teeth, calculated as total area using digital histomorphometry analysis of the five most central sections from each experimental cavity, was significantly higher (p<0.005) than in calcium hydroxide treated control specimens Conclusion These results demonstrate the potential of EMD as a biologically active pulp dressing agent that specifically induce pulpal wound healing and dentine formation in pulpotomized teeth without affecting the normal function of the remaining pulp.

Materials and Methods

Surgical Procedure

A total number of 36 permanent lower incisor teeth from 11 adult miniature swine with a mean age of 3 years were used. Animals were divided into three groups. Observation times were three weeks (n=4 teeth/EMD treated, n=4 teeth/Ca(OH)2 treated), four weeks (n=7 teeth/EMD treated, n=7 teeth/Ca(OH)2 treated) and eight weeks (n=7 teeth/EMD treated, n=7 teeth/Ca(OH)2 treated), respectively. The animals were anaesthetized with an injection of 10 ml Ketalar® i.m. and 8 ml pentobarbital i.v. The surgical sites were infiltrated with the local anaesthetic Xylocain® (20 mg/ml) adrenalin (12.5 µg/ml). In order to facilitate cavity preparation during pulpotomy, the incisal crowns were removed at the gingival cervices. Subsequently, access cavities were prepared through the occlusal surface with a diamond bur used in a high-speed drill. Finally, a round steel bur was used in a slow-speed to expose the pulp and remove it. During all steps of the operative procedure, the tooth and cutting instruments were irrigated with sterile saline spray. Bleeding was controlled with sterile cotton pellets. The exposed pulp tissue was then covered with EMD (EMDOGAIN® Gel; 30 mg/ml in propylene-glycol-alginate (PGA); BIORA AB, Malmö, Sweden) or calcium hydroxide (Dycal®: DENTSPLY, Konstanz, Germany). Subsequently each cavity was filled with glass-ionomer cement (GC Fuji II®: GC Corporation, Tokyo, Japan) to ensure cavity sealing and restore dental function.

Histological Examination

At 3, 4 or 8 weeks after surgery the animals were sacrificed by an intra-cordial bolus injection of 50 ml sodium pentobarbital in ethanol. Following euthanasia all experimental teeth were extracted and fixed in cold 4% neutral buffered formaldehyde for 24 hours. The specimens were then demineralized in 12.5% EDTA and subsequently embedded in paraffin. After longitudinal serial sectioning (6 µm) every second section was stained with hematoxylin and eosin. Series of sections containing pulp tissue were then analyzed in a light microscope equipped for histometry.

Quantitative Analyses of New Hard Tissues

The amount of new hard tissue formed subjacent to the cavity was assessed in the central sections (n=5) from each experimental tooth. The areas covered by newly formed hard tissue in these sections were measured using digital, histometry equipment (Olympus Microimage®: Media Cybernetics, Maryland, U.S.A.). The limit for histometric analysis was arbitrarely set to 2 mm apically from the bottom of the preparation of experimental cavities.

Results

Figure 11A:
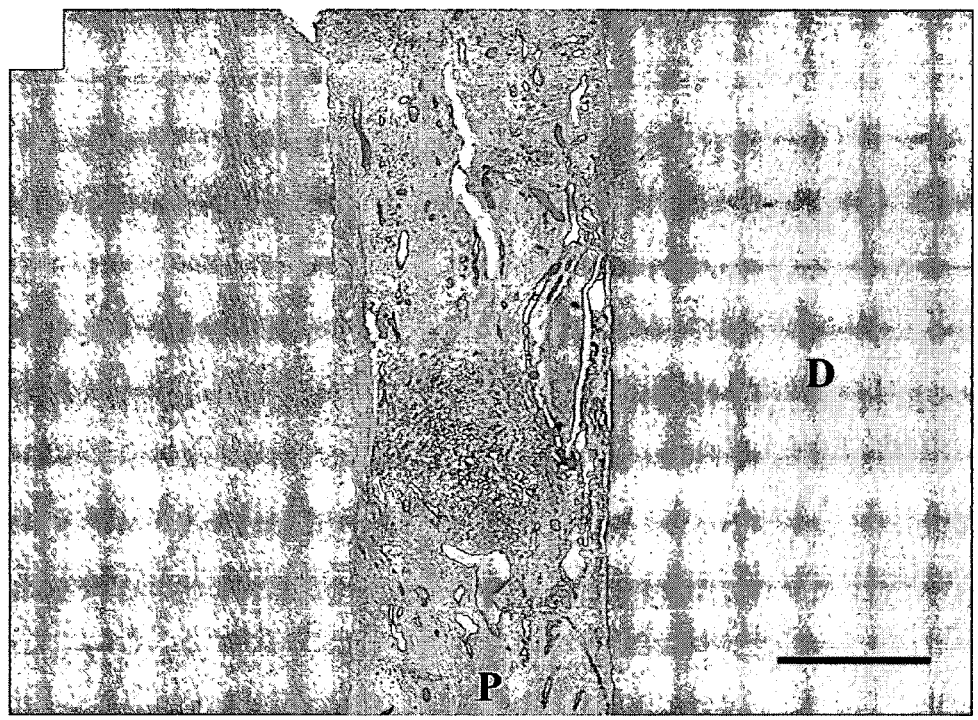
Figure 11B:
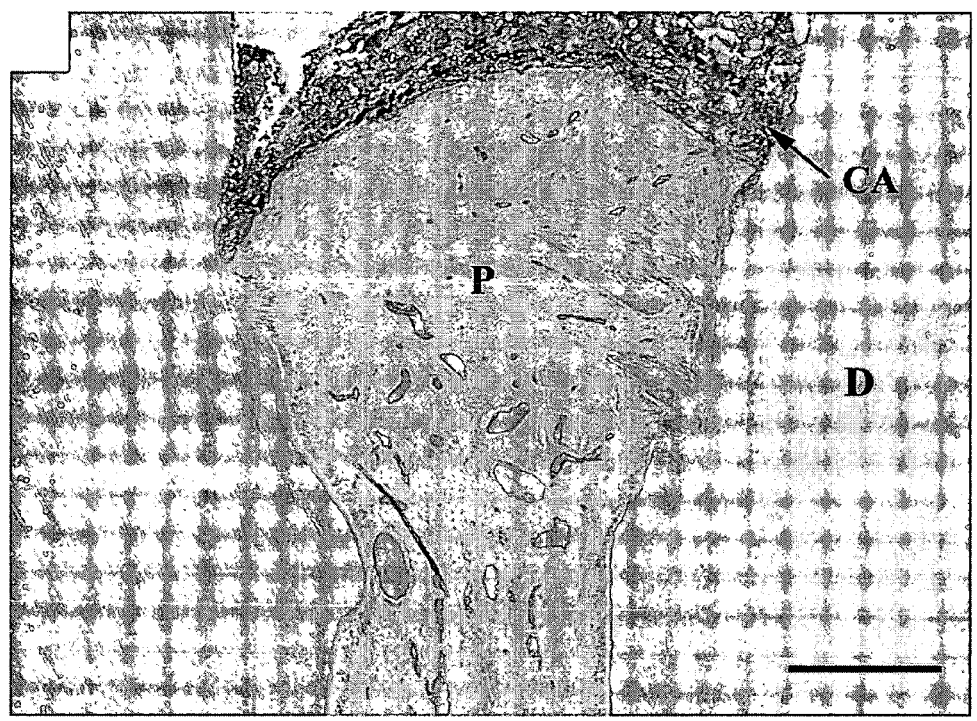

Three weeks after application of EMD, an acellular tissue overlaying a zone with a moderate inflammatory cell infiltrate was observed at the pulpal wound in histological sections. A marked increase in angiogenesis was evident in the deeper part of the pulp tissue below the application sites (FIGS. 10a, 11a), and in half of the teeth small islands consisting of an osteodentine-like tissue were observed forming subjacent to the amputation site. The histological picture from EMD treated teeth closely resembled that of normal wound healing including the formation of a scab, a moderate inflammatory infiltrate beneath the injury and a local increase in angiogenesis and cell proliferation. None of the teeth treated with EMD showed signs of irreversible pulp damage, partial necrosis or infections. At this stage the control teeth treated with Ca(OH)2 exhibited a distinct liquefaction necrosis of the tissue close to the capping material. In most control teeth a zone of newly formed pre-dentine was observed forming onto and along the circumpulpal dentine wall subjacent to the amputation site. In the brim between the vital pulp tissue and the necrotized superficial layer some angiogenetic activity was present (FIGS. 10d, 11b). The situation in the control teeth treated with Ca(OH)2 most closely resembles that of a chemical bum exhibiting a superficial necrotic tissue at the wound site with only low cellular activity in the subjacent region.

Figure 12A:
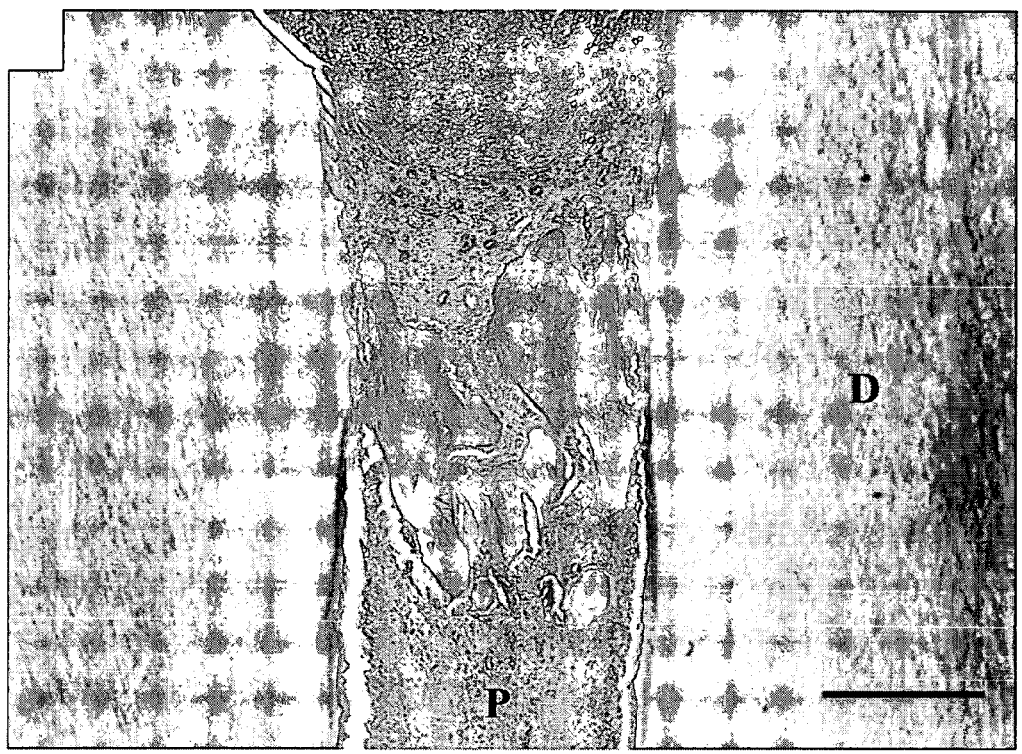
Figure 12B:
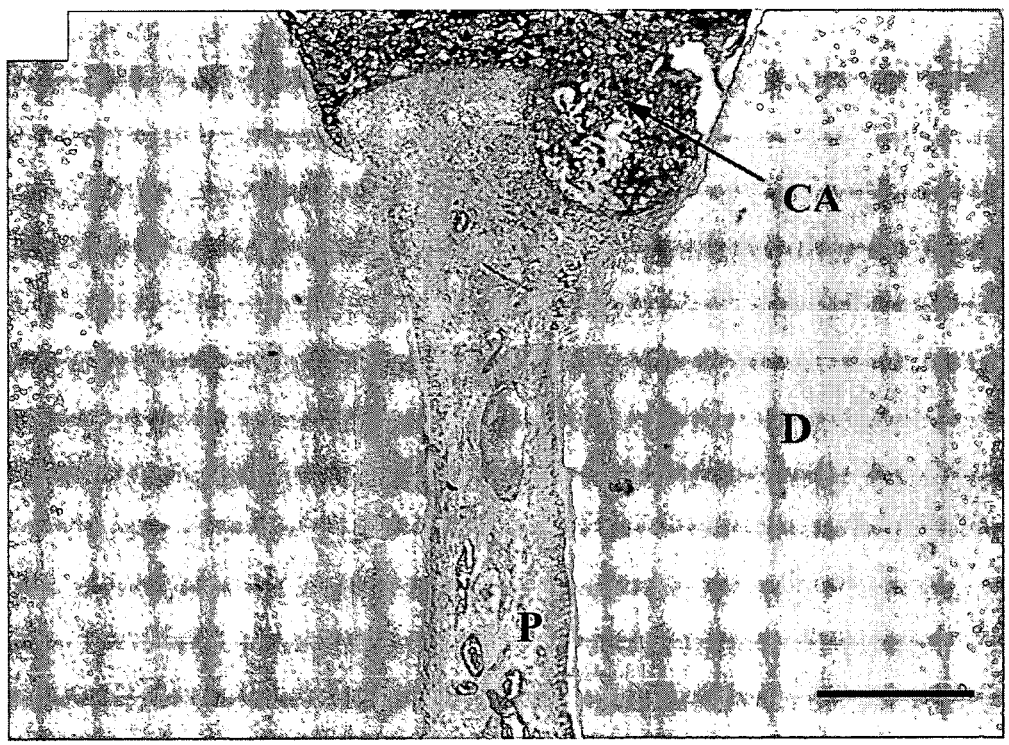
Figure 13A:

In teeth extracted for sectioning four weeks after surgery and EMD application, moderate amounts of a new dentine-like tissue bridged the full width of the cavities at the interface between the wounded and the unharmed pulp tissue. A web of new hard-tissue islets in close contact with newly formed odontoblast-like cells surrounded the newly formed dentine bridge on the apical side (FIGS. 10b, 12a). In calcium hydroxide control teeth extracted at four weeks post surgery, new hard tissue resembling secondary dentine formed only onto the root canal wall and no bridging was observed in these teeth at this timepoint. This newly formed secondary dentine formed directly onto and along the pre-existing dentine walls leading to a significant narrowing of the pulp chamber (FIGS. 10e, 12b). Six out of seven teeth extracted eight weeks after EMD application exhibited extensive new formation of dentine in the form of complete dentine bridges that efficiently sealed off the remaining healthy pulp from the experimental defects including the "scab" tissue. The pulp tissue subjacent to the bridges appeared healthy with no inflammation present and with no internal resorptions (FIGS. 10c, 13a). The last tooth in this group showed an extensive amount of reparative dentine formation, although the defect was not yet completely bridged (Table 1). In comparison, five of the seven control teeth treated with calcium hydroxide showed complete closure of the pulpal wound. In two of these five teeth, the new secondary dentine formation was at the expense of the root pulp chamber causing severe narrowing of the root canal. In the remaining two cases without complete closure of the wound, one exhibited a tortuous root canal, while the last one showed almost no new dentine formation, but rather a moderate inflammation infiltrate and signs of internal resorptions (p<0.005, Table 1).

TABLE 1

|  | EMD | Ca(OH)$_2$ |
| --- | --- | --- |
| Defect Size (mm) | 1.112 ± 0.167 | 1.078 ± 0.421 |
| Complete Dentine Bridge | 6/7 | 5/7 |
| Thickness of Dentine Bridge(mm) | 1.292 ± 0.349 | 0.752 ± 0.276 |
| Dentine area (mm$^2$) | 1.513 ± 0.731 | 0.822 ± 0.616 |

Defect size, frequency of complete dentine bridges, mean thickness (± S.D.) of complete dentine bridges, and mean area (± S.D.) of newly formed dentine after 8 weeks for EMD and Ca(OH)$_2$ treatment of exposed pulps.

Figure 13B:
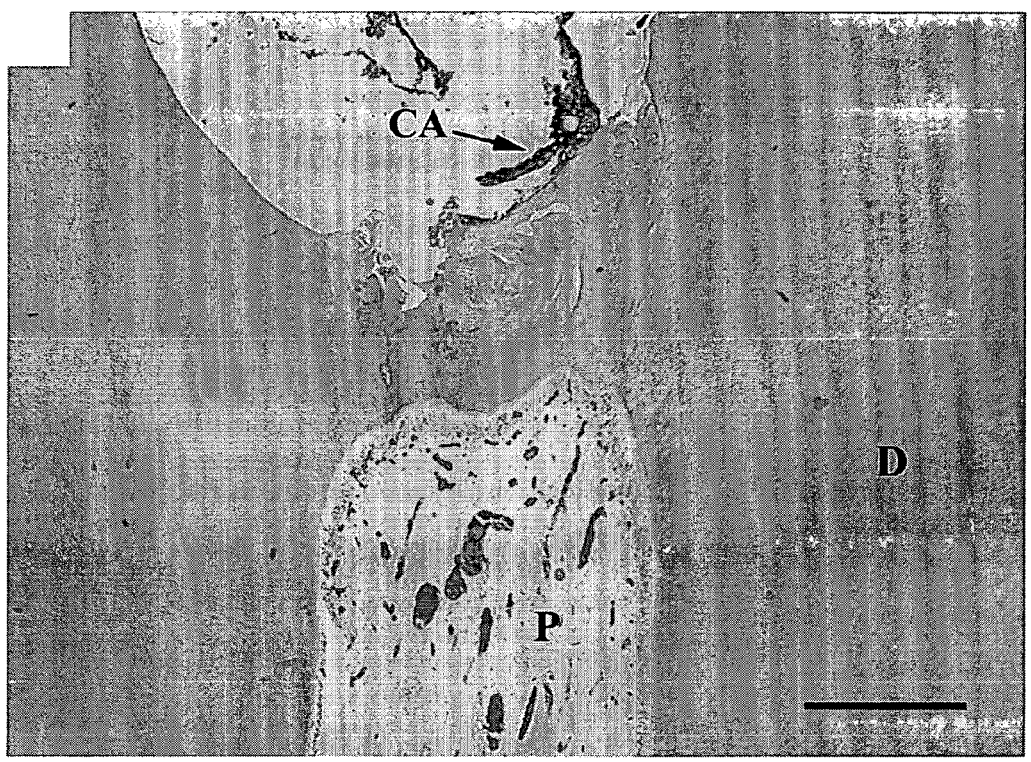

When the thickness of the dentine bridges formed in control and EMD treated teeth after eight weeks was assessed by histomorphometry the mean thickness of the dentine-like tissue bridging the defects was significantly larger in EMD treated teeth than in the control group (p<0.001) (FIGS. 10f, 13b and Table 1). Also the total amount of newly formed mineralized tissue in the EMD treated teeth, calculated as total area using digital histomorphometry analysis of the five most central sections from each experimental cavity, was significantly higher (p<0.005) than in calcium hydroxide treated control specimens (Table 1). In fact, eight weeks after surgery the amount of newly formed hard tissue in the EMD treated teeth was more than twice that of the controls.

LIST OF REFERENCES

L. Hammarström, J. Clin. Periodontol. 24, 1997, pp. 658-668

A. R. Ten Cate, *Oral Histology. Development, Structure and Function,* 5th Ed., Mosby 1998, pp. 150-196

Ten Cate: Oral Histology, 1994; Robinson: Eur. J. Oral Science, January 1998, 106 Suppl. 1:282-91

Janson, J-C & Rydén, L. (Eds.), Protein purification, VCH Publishers 1989 and Harris, ELV & Angal, S., Protein purification methods—A practical approach, IRL Press, Oxford 1990

Sambrook, J. et al.: Molecular Cloning, Cold Spring Harbor Laboratory Press, 1989

Fincham et al. in J. Struct. Biol. 1994 March-April; 112(2): 103-9 and in J. Struct. Biol. 1995 July-August; 115(1): 50-9

Gestrelius S, Andersson C, Johansson A C, Persson E, Brodin A, Rydhag L, Hammarstrom L (1997). Formulation of enamel matrix derivative for surface coating. Kinetics and cell colonization. J Clin Periodontol:678-684

Lyngstadaas S P, Lundberg E, Ekdahl H, Andersson C and Gestrelius S (2001). Autocrine growth factors in human periodontal ligament cells cultured on enamel matrix derivative. J Clin Periodontol, February; 28(2):181-8

Remington's Pharmaceutical Sciences" and "Encyclopedia of Pharmaceutical Technology", edited by Swarbrick, J. & J. C. Boylan, Marcel Dekker, Inc., New York, 1988

Remington's Pharmaceutical Sciences", 18th Edition, Mack Publishing Company, Easton, 1990

The invention claimed is:

1. A method of promoting one or more of regeneration of secondary dentin, formation of reparative dentin, or formation of osteodentin in a mammal, the method comprising administering to exposed vital dental pulp tissue of said mammal an active enamel substance comprising enamel matrix proteins selected from the group including one or more of enamelins, amelogenins, amelins, ameloblastin, sheathlin, tuftelins, dentinsialoprotein, and dentinsialophosphoprotein in an amount sufficient to promote one or more of regeneration of secondary dentin or formation of reparative dentin or formation of osteodentin.

2. The method of claim 1, wherein the step of administering the active enamel substance comprises causing the active enamel substance to contact the mammal's vital dental pulp tissue.

3. The method according to claim 1, wherein said vital dental pulp tissue is comprised in erupted teeth.

4. The method according to claim 1, wherein the mammal is human.

5. The method according to claim 4, wherein the human is older than about 12 years old.

6. The method of claim 1, further comprising the step of applying a filling material to the exposed vital dental pulp of said mammal following a dental procedure involving exposure of the mammal's vital dental pulp tissue.

7. The method according to claim 1, wherein the active enamel substance is of porcine origin.

8. The method according to claim 1, wherein the active enamel substance is of synthetic origin.

9. The method according to claim 1, wherein the active enamel substance is an enamel matrix or an enamel matrix protein.

10. The method according to claim 1, wherein the active enamel substance comprises at least two substances selected from the group consisting of amelogenins, enamelins, amelins, ameloblastin, sheathlin, tuftelins, tuft proteins, serum proteins, salivary proteins, dentinsialoprotein, and dentinsialophosphoprotein.

11. The method according to claim 1, wherein the active enamel substance comprises amelogenins.

12. The method according to claim 1, wherein the active enamel substance has a molecular weight of at most about 120 kDa, as determined by SDS electrophoresis.

13. The method according to claim 1, wherein the active enamel substance has a molecular weight of at most about 100 kDa, as determined by SDS electrophoresis.

14. The method according to claim 1, wherein the active enamel substance has a molecular weight of at most about 90 kDa, as determined by SDS electrophoresis.

15. The method according to claim 1, wherein the active enamel substance has a molecular weight of at most about 80 kDa, as determined by SDS electrophoresis.

16. The method according to claim 1, wherein the active enamel substance has a molecular weight of at most about 70 kDa, as determined by SDS electrophoresis.

17. The method according to claim 1, wherein the active enamel substance has a molecular weight of at most about 60 kDa, as determined by SDS electrophoresis.

18. The method according to claim 1, wherein the active enamel substance has a molecular weight below about 60 kDa, as determined by SDS electrophoresis.

19. The method according to claim 1, wherein the active enamel substance has a molecular weight up to about 40 kDa, as determined by SDS electrophoresis.

20. The method according to claim 1, wherein the active enamel substance has a molecular weight between 5 kDa and 25 kDa, as determined by SDS electrophoresis.

21. The method according to claim 1, wherein the active enamel substance has a molecular weight of about 25 kDa, as determined by SDS electrophoresis.

22. The method according to claim 1, wherein the active enamel substance has a molecular weight of about 20 kDa, as determined by SDS electrophoresis.

23. The method according to claim 1, wherein the active enamel substance has a molecular weight of about 5 kDa, as determined by SDS electrophoresis.

24. The method according to claim 1, wherein the active enamel substance comprises a mixture of active enamel substances having different molecular weights.

25. The method according to claim 1, wherein the active enamel substance includes one or more of amelogenin, amelin, tuftelin and dentinsialoprotein having a molecular weight below about 60 kDa, as determined by SDS electrophoresis.

26. The method according to claim 1, wherein at least a part of the active enamel substance is in the form of aggregates or after application in viva is capable of forming aggregates.

27. The method according to claim 26, wherein the aggregates have a molecular weight from about 5 kDa to about 40 kDa, as determined by SDS electrophoresis.

28. The method according to claim 26, wherein the aggregates have a particle size from about 20 nm to about 1 μm.

29. The method according to claim 1, wherein a pharmaceutical composition comprising the active enamel substance is administered to the mammal.

30. The method according to claim 29, wherein the pharmaceutical composition comprises a pharmaceutically acceptable excipient.

31. The method according to claim 30, wherein the pharmaceutically acceptable excipient is propylene glycol alginate.

32. The method according to claim 29, wherein the pharmaceutical composition comprises about 30 mg/ml active enamel substance in propylene glycol alginate.

33. The method according to claim 1, wherein the amount of active enamel substance applied to the mammal's vital dental pulp tissue is an amount of total protein per $mm^2$ of dental pulp tissue corresponding to from 0.005 $mg/mm^2$ to 5.0 $mg/mm^2$.

34. The method according to claim 33, wherein the amount of active enamel substance applied to the mammal's vital dental pulp tissue is an amount of total protein per $mm^2$ of dental pulp tissue corresponding to from 0.01 $mg/mm^2$ to 3.0 $mg/mm^2$.

35. The method according to claim 1, wherein the active enamel substance is applied at a concentration between 0.01 mg/ml to 40 mg/ml.

36. The method according to claim 1, wherein the active enamel substance is applied at a concentration between 0.1 mg/ml to 30 mg/ml.

37. The method according to claim 1, wherein the active enamel substance has a protein content from about 0.05% w/w to 100% w/w.

* * * * *

UNITED STATES PATENT AND TRADEMARK OFFICE
CERTIFICATE OF CORRECTION

| | | |
|---|---|---|
| PATENT NO. | : 7,304,030 B2 | Page 1 of 1 |
| APPLICATION NO. | : 09/885725 | |
| DATED | : December 4, 2007 | |
| INVENTOR(S) | : Lyngstadaas | |

It is certified that error appears in the above-identified patent and that said Letters Patent is hereby corrected as shown below:

Title Page Item (54) And Col.1, Ln 1 & 2,

The title of the invention should read:
 --MATRIX PROTEIN COMPOSITIONS FOR DENTIN REGENERATION Col. 25, line 11
In claim 26, the third line should read:
 --...aggregates or after application in vivo is capable of forming…--

Signed and Sealed this

Fifteenth Day of April, 2008

JON W. DUDAS
*Director of the United States Patent and Trademark Office*